US010918671B2

(12) United States Patent
Hattori et al.

(10) Patent No.: US 10,918,671 B2
(45) Date of Patent: *Feb. 16, 2021

(54) METHOD OF CONSTRUCTING MASSES OF MYOCARDIAL CELLS AND USE OF THE MYOCARDIAL CELL MASS

(71) Applicants: DAIICHI SANKYO COMPANY, LIMITED, Tokyo (JP); HEARTSEED INC., Tokyo (JP)

(72) Inventors: Fumiyuki Hattori, Osaka (JP); Keiichi Fukuda, Tokyo (JP)

(73) Assignees: DAIICHI SANKYO COMPANY, LIMITED, Tokyo (JP); HEARTSEED INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/798,650

(22) Filed: Jul. 14, 2015

(65) Prior Publication Data

US 2015/0366918 A1    Dec. 24, 2015

Related U.S. Application Data

(63) Continuation of application No. 12/668,136, filed as application No. PCT/JP2008/064168 on Jul. 31, 2008, now Pat. No. 9,109,205.

(30) Foreign Application Priority Data

Jul. 31, 2007  (JP) .............................. JP2007-200246
Feb. 27, 2008  (JP) .............................. JP2008-046772

(51) Int. Cl.
| | |
|---|---|
| C12N 5/00 | (2006.01) |
| A61K 35/34 | (2015.01) |
| A61L 27/38 | (2006.01) |
| C12N 5/077 | (2010.01) |
| A61K 35/12 | (2015.01) |

(52) U.S. Cl.
CPC .......... *A61K 35/34* (2013.01); *A61L 27/3826* (2013.01); *A61L 27/3895* (2013.01); *C12N 5/0657* (2013.01); *A61K 35/12* (2013.01); *A61L 2430/20* (2013.01); *C12N 2500/25* (2013.01); *C12N 2500/90* (2013.01); *C12N 2500/99* (2013.01); *C12N 2501/105* (2013.01); *C12N 2501/11* (2013.01); *C12N 2501/115* (2013.01); *C12N 2501/117* (2013.01); *C12N 2501/12* (2013.01); *C12N 2501/125* (2013.01); *C12N 2501/13* (2013.01); *C12N 2501/135* (2013.01); *C12N 2501/235* (2013.01); *C12N 2501/33* (2013.01); *C12N 2501/998* (2013.01); *C12N 2506/00* (2013.01); *C12N 2506/02* (2013.01); *C12N 2506/03* (2013.01); *C12N 2506/04* (2013.01); *C12N 2506/45* (2013.01)

(58) Field of Classification Search
USPC ................. 435/325; 424/93.1, 93.2
See application file for complete search history.

(56) References Cited

U.S. PATENT DOCUMENTS

| | | | |
|---|---|---|---|
| 8,623,649 B2 * | 1/2014 | Hattori ............. | G01N 33/56966 435/352 |
| 2005/0214938 A1 | 9/2005 | Gold et al. | |
| 2005/0214939 A1 | 9/2005 | Gold et al. | |

FOREIGN PATENT DOCUMENTS

| | | | |
|---|---|---|---|
| EP | 1674562 A1 | | 6/2006 |
| JP | WO 2005/033298 | * | 4/2005 |
| JP | WO 2006/022377 | * | 3/2006 |
| WO | WO-2005033298 A1 | | 4/2005 |
| WO | WO 2005/090558 | * | 9/2005 |
| WO | WO-2005090558 A1 | | 9/2005 |

OTHER PUBLICATIONS

Narsinh et al., Molecular Therapy, 2001, vol. 9, No. 4, p. 635-637.*
Honda (Biochem. & Biophysical Res. Comm., 2006, vol. 351, p. 877-882).*
Muller (FASEB, 2000, vol. 14, p. 2540-2548).*
Masuda (Regenerative Med., 2005, Supplemental vol. 4, p. 201, abstract P2-074).*
Masuda (Regenerative Med., 2005, Supplemental vol. 4, p. 201, abstract P2-074) translation.*
Miyagawa (Transplantation, 2005, vol. 80, p. 1586-1595).*
Shimizu (Circ. Res., 2002, vol. 90, e40-e48).*
Hattori (WO 2006/022377) machine translation 2016.*
Fukuda (WO 2005/033298) machine translation, 2016.*
International Preliminary Report on Patentability dated Feb. 24, 2010, in International Application No. PCT/JP2008/064168.
International Search Report dated Sep. 16, 2008 in International Application No. PCT/JP2008/064168.
Masuda et al. P2-074, Regenerative Medicine, vol. 4, Suppl. P. 201 (in Japanese) (2005).
Honda et al., "N-cadherin is a useful marker for the progenitor of cardiomyocytes differentiated from mouse ES cells in serum-free condition," Biochemical and Biophysical Research Communications 351 (2006). pp. 877-882.
Xu et al., "Cardiac bodies: A Novel Culture Method for Enrichment of Cardiomyocytes Derived from Human Embryonic Stem Cells," Stem Cells and Development, vol. 15, (2006), pp. 631-639.

(Continued)

*Primary Examiner* — Michael C Wilson
(74) *Attorney, Agent, or Firm* — Faegre Drinker Biddle & Reath LLP

(57) ABSTRACT

The object of the present invention is to improve the post-transplantation engraftment rate of cardiomyocytes that have been purified to such an extent that they are free from non-cardiomyocytes and any components derived from other species.

To solve this problem, the present inventors studied the possibility of constructing cell masses from the purified cardiomyocytes. As a result, they revealed that the stated problem could be solved by providing a method of preparing cell masses of cardiomyocytes derived from pluripotent stem cells, characterized in that cell masses of aggregated cells containing cardiomyocytes that had been differentiated and induced from pluripotent stem cells were dispersed to single cells to thereby obtain purified cardiomyocytes, which were then cultured in a culture medium under serum-free conditions so that they were reaggregated.

14 Claims, 25 Drawing Sheets

(56) References Cited

OTHER PUBLICATIONS

Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, Feb. 22, 2002. vol. 90 pp. 1-9.
Gao et al., "Transplantation of fetal cardiomyocyte regenerates infarcted myocardium in rats," Zhongnua Yi Xue Za Zhi, Oct. 25, 2003, vol. 83, No. 20, pp. 1818-1822 (English Abstract).
Caspi et al., "Tissue Engineering of Vascularized Cardiac Muscle from Human Embryonic Stem Cells," Circulation Research, Feb. 2, 2007, pp. 263-272.
Just et al., "Formation of Three-Dimensional Fetal Myocardial Tissue Cultures from Rat for Long-Term Cultivation," Developmental Dynamics, 2006, vol. 235, No. 2200-2209.
Soonpaa et al., "Formation of Nascent Intercalated Disks Between Grafted Fetal Cardiomyocytes and Host Myocardium," Science, vol. 264, Apr. 1, 1994, pp. 98-101.
Baba et al., "Flk1+ cardiac stem/progenitor cells derived from embryonic stem cells improve cardiac function in a dilated cardiomyopathy mouse model," Cardiovascular Research, vol. 76, 2007. pp. 119-131.
Tomescot et al., "Differentation In Vivo of Cardiac Committed Human Embryonic Stem Cells in Postmyocardial Infarcted Rats," Stem Cells, 2007, vol. 25, pp. 2200-2205.
Huber et al., "Identification and selection of cardiomyocytes during human embryonic stem cell differentiation," The FASEB Journal, vol. 21, Aug. 2007, pp. 2551-2563 .
Kolossov et al., "Engraftment of engineered ES cell-derived cardiomyocytes but not BM cells restores contractile function to the infarcted myocardium," JEM, Sep. 5, 2006, vol. 203, pp. 2315-2327.
Xu et al., "Human Embryonic Stem Cell-Derived Cardiomyocytes Can be Maintained in Defined Medium without Serum," Stem Cells Dev., vol. 15, No. 6, pp. 931-941 (2006).
Shimizu et al., "Polysurgery of cell grafts overcomes diffusion limits to produce thick, vascularized myocardial tissues," The FASEB Journal, vol. 20, Apr. 2006, pp. 708-710.
Koike et al., Cytotechnology, 2005, vol. 47, pp. 3-10.
Lau et al., Tissue Cell, 1993, vol. 25, No. 3, pp. 465-480, Abstract Only.
Miyagawa et al., Transplantation, 2005, vol. 80, pp. 1586 and 1593.
Sachinidis et al., Cell Physiol. Biochem., 2003, vol. 13, No. 6 pp. 423-426, Abstract Only).
Patel et al., Developmental Dynamics, 2005, vol. 233, pp. 20-28.
Dell' Era et al., Circ. Res., 2003. vol. 93, pp. 414-420.
Supplementary European Search Report dated Nov. 18, 2011 in EP Application No. 08792275.3.
Hattori et al., "Nongenetic method for purifying stem cell-derived cardiomyocytes", Nature Methods, vol. 7, No. 1, Jan. 2010., pp. 61-66.
Yu, et al., "Pluripotent stem cell lines", Genes & Development, 22, 2008, 1987-1997.
Office Action of CA 2,690,610 dated Feb. 6, 2012.
Office Action of CA 2,690,610 dated Mar. 6, 2013.
Office Action of CA 2,690,610 dated Feb. 6, 2014.
Office Action of CA 2,690,610 dated Dec. 2, 2014.
Office Action of CA 2,690,610 dated Feb. 2, 2016.
Office Action of CA 2,690,610 dated Mar. 17, 2017.
Office Action of CA 2,690,610 dated Oct. 18, 2018.
Mitcheson et al., "Cultured adult cardiac myocytes: Future applications, culture methods, morphological and electrophysiological properties," Cardiovascular Research, Vo. 39, 1998, pp. 280-300.
Oldenburg et al., "Bradykinin induces mitochondrial ROS generation via NO, cGMP, PKG, and mitoK$_{ATP}$ channel opening and leads to cardioprotection," Am. J. Physiol Heart Circ. Physiol 286:H468-76, 2004.
Messina et al., "Isolation and Expansion of Adult Cardiac Stem Cells From Human and Murine Heart," Circ Res. 2004, 95:911-921.
Tang et al., "A novel two-step procedure to expand Sca-1+ cells clonally," Biochem Biophys Res Commun, Aug. 10, 2007, vol. 359, pp. 877-883.
Zweigerdt et al., "Generation of confluent cardiomyocyte monolayers derived from embryonic stem cells in suspension: a cell source for new therapies and screening strategies," Cytotherapy 2003, vol. 5, pp. 399-413.

* cited by examiner

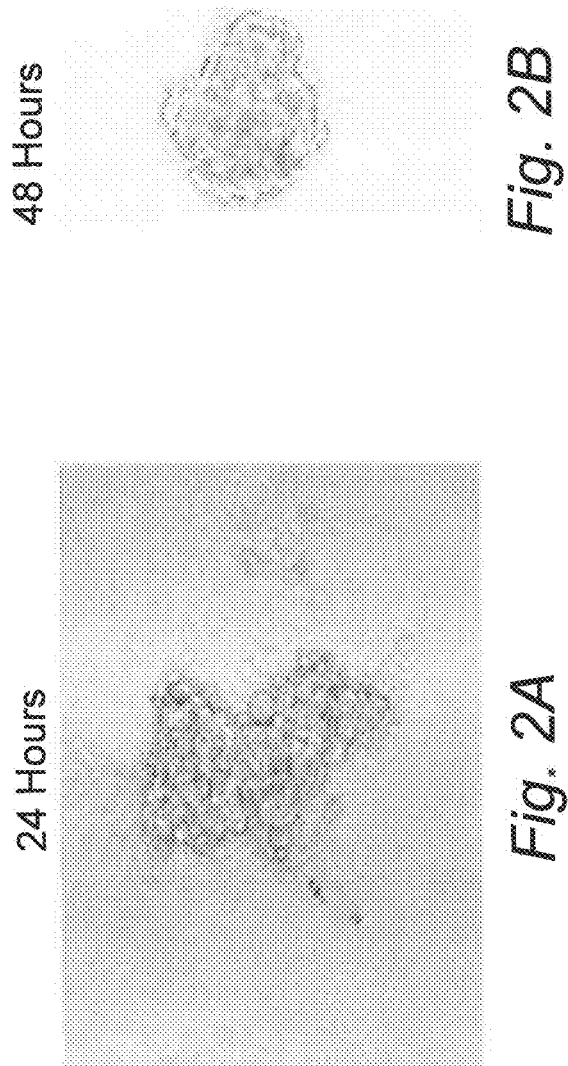

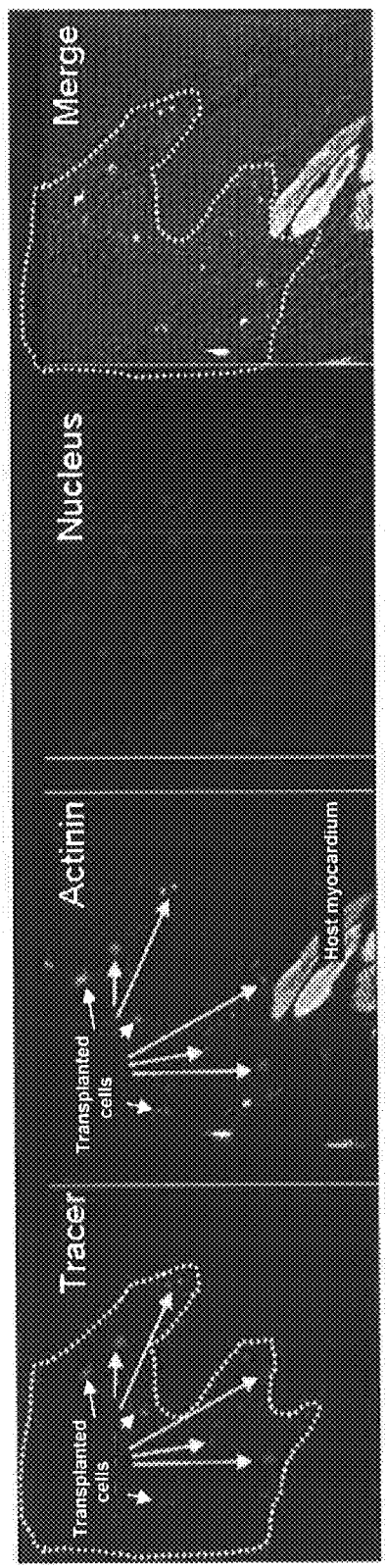

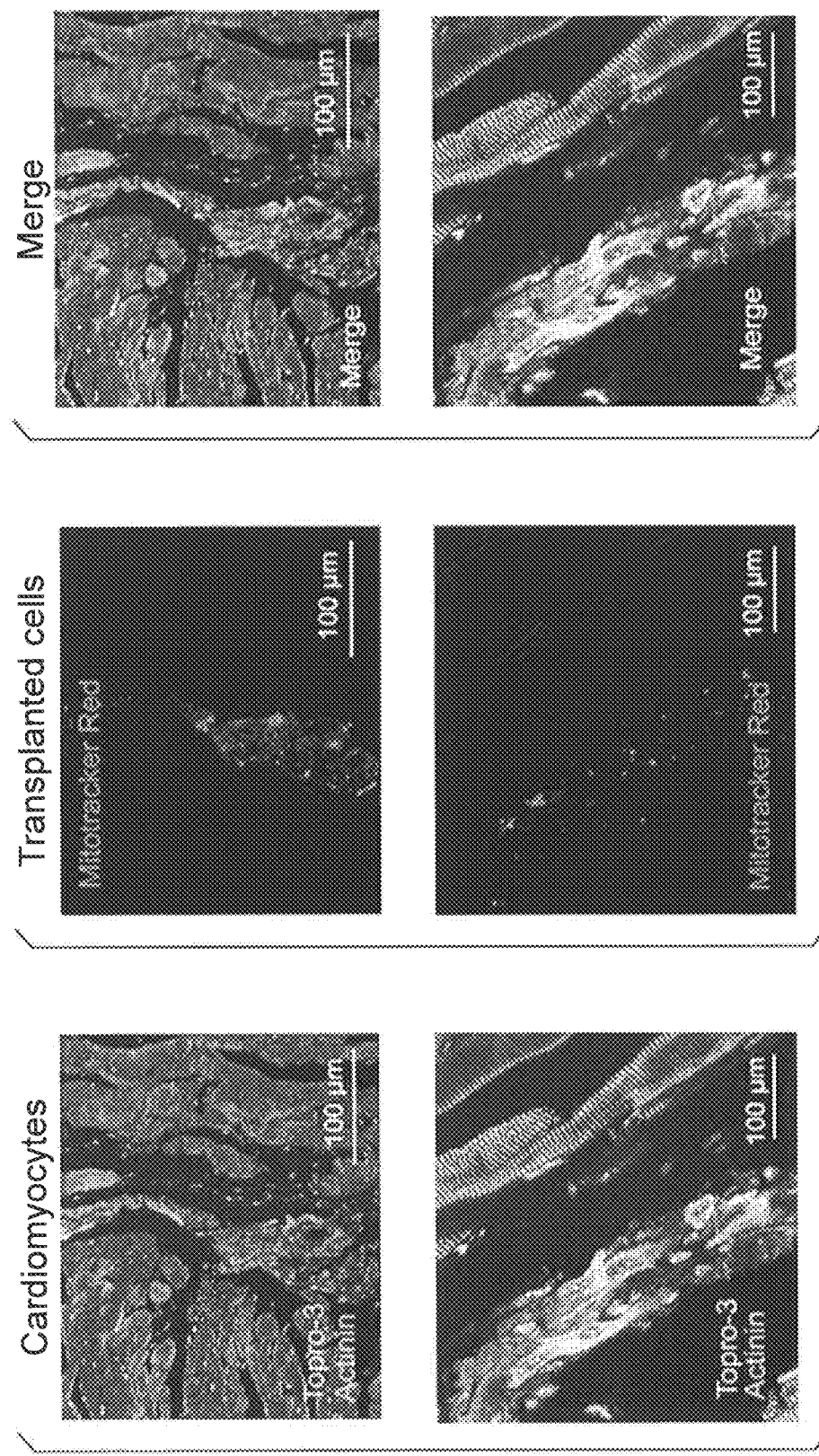

METHOD OF CONSTRUCTING MASSES OF MYOCARDIAL CELLS AND USE OF THE MYOCARDIAL CELL MASS

CROSS REFERENCE TO RELATED APPLICATIONS

This application is a Continuation of copending application Ser. No. 12/668,136, filed Mar. 4, 2010, which is a National Stage of International Application No. PCT/JP2008/064168, filed Jul. 31, 2008, which claims priority to JP 2007-200246, filed Jul. 31, 2007, and JP 2008-046772, filed Feb. 27, 2008.

TECHNICAL FIELD

The present invention relates mainly to a method of preparing cell masses by aggregating purified cardiomyocytes derived from pluripotent stem cell obtained by dispersing to single cells, as well as a method of treating cardiac disease by causing the prepared cell masses of cardiomyocytes to be engrafted in the cardiac tissue, and a method of preparing sheets of cell masses using the cell masses of cardiomyocytes.

BACKGROUND ART

Cardiomyocytes in adults have lost the proliferating activity and cardiac transplantation is the only way to treat serious cardiac diseases such as myocardial infarction and cardiomyopathy. In fact, however, owing to a problem of the lack of cardiac tissue donors, there is a pressing need to develop a method of treatment other than cardiac transplantation.

In contrast, use of cardiomyocytes prepared outside the living body to supply with them part of the diseased cardiomyocytes is anticipated to become the most promising way to save patients who have to depend on cardiac transplantation. This approach of treatment is called cell therapy on the heart, To bring this therapy into reality, various trials and errors have been conducted. The methods under review include: using cardiomyocytes or skeletal myoblasts and bone marrow cells or the like that have been extracted from fetuses, neonates or adults; using differentiated embryonic stem cells; and obtaining the stem cells (such as somatic stem cells) which are suggested to exist in the living body has been suggested, and inducing their differentiation (Non-Patent Document 1: Zhonghua Yi Xue Za Zhi 2003, 83, 1818-22).

These methods can be divided into two approaches. One approach involves transplanting cardiomyocytes as cells and in this method, the cardiomyocytes dispersed to single cells are directly injected into a tissue via injection needle (this method is hereinafter referred to as an "injection method"). The other approach involves constructing a tissue or an organ outside the living body (which is hereinafter referred to as a "tissue engineering method") and this artificial tissue or organ is transferred into the body for treatment.

Various attempts have, been made to implement the tissue engineering method and they include: 1) a method in which cardiomyocytes are forms in sheet-like structure, which are then attached onto a tissue (Non-Patent Document 2: Circulation Research 2002, 90(3):e-40); 2) a method in which cardiomyocytes and non-cardiomyocytes are mixed in the same proportions as they are in the cardiac tissue and a three-dimensional structure formed of the mixture is used to replace the tissue; 3) a method in which a three-dimensional structure is formed of the cardiomyocytes dispersed to single cells, with a vascular structure being further constructed, and the three-dimensional structure is substituted for the tissue; and 4) a method in which, rather than replacing the cardiac tissue, a new auxiliary organ that assists in the inherent organ function is transplanted to a site ectopically (Non-Patent Document 3: Circulation Research 2007 2, 100: 263-272).

However, at the present stage where various trials and errors are under way toward clinical therapeutic application, no method has yet exhibited practical data. This is because transplanting cardiomyocytes to the heart involves several problems, such as the inclusion of cells other than cardiomyocytes, low engraftment rate of the transplanted cardiomyocytes, and the inability to exclude components derived from other species.

To use cardiomyocytes as cell masses in transplantation, methods are known that are capable of constructing cell masses including fetal or neonatal rodent cardiomyocytes and, according to a recent report, cell masses were constructed using whole cells (including non-cardiomyocytes) that were derived from the fetal heart (Non-Patent Document 4; Developmental Dynamics 235; 2200-2209, 2006). As regards the transplantation of cardiomyocytes, a ease has been reported where fetal mouse cardiomyocytes were transplanted into the hearts of adult mice, which were confirmed to be engrafted (Non-Patent Document Science 1994, 264 (5155): 98-101). However, this method of the transplantation of cardiomyocytes involved the use of whole cells to which the whole fetal hearts were dispersed by means of collagenase, so the transplanted cells were composed of a cell population comprising a mixture of cardiomyocytes and non-cardiomyocytes. It is also known that non-purified cardiomyocytes derived from the living body can be transplanted to the heart (Non-Patent Document 5: Science 1994, 264(5155): 98-101; and Non-Patent Document 1: Zhonghua Yi Xue Za Zhi 2003, 83, 1818-22).

Also known is a method in which, in the process of differentiation of embryoid bodies from ES cells, the embryoid bodies are incompletely treated with a proteolytic enzyme, whereupon a population comprising cell masses that are rich in cardiomyocytes and those which are not is obtained and then is subjected to density gradient centrifugation, thereby obtaining cell masses that contain up to about 70% of cardiomyocytes (Patent Document 1: US 2005-0214938 A).

However, each of those methods involves the use of a cell population that also contains cells other than cardiomyocytes and contamination of such cells other than cardiomyocytes may have the potential to cause serious unpredictable side effects that may threaten the life of a patient after transplantation. Under the circumstances, it is considered necessary that cardiomyocytes to be subjected to transplantation therapy should be used after purification.

Several reports have described achievements in transplanting unpurified, ES cell-derived cardiomyocytes to the heart and allowing them to be engrafted thereafter (Non-Patent Document 6; Cardiovasc Res. 2007 May 17; Non-Patent Document 7: Stem Cells. 2007 May 31; and Non-Patent Document 8: FASEB J. 2007 Apr. 13). According to a recent paper, however, which discussed purifying ES cell-derived cardiomyocytes and injecting theirs into the heart, the engraftment rate of the transplanted cardiomyocytes was extremely low and no cardiomyocytes were found to be engrafted (i.e., those survived within the host organ and remained adherent in it for an extended period of time); as it turned out, the purified, ES cell-derived cardiomyocytes were not able to be engrafted after they were transplanted into an individual (the living body) (Non-Patent Document 9: J Exp Med. 2006; 203: 2315-27.)

This report has brought light to the difficulty in causing purified cardiomyocytes to be engrafted after transplantation. In order to solve this problem, a method was discovered in the same report that involved transplanting the ES cell-derived cardiomyocytes in admixture with mouse embryonic fibroblasts with a tor the purpose of enhancing their engraftment rate after transplantation (Non-Patent Document 9: J Exp Med. 2006 Oct. 2; 203(10): 2315-27). This shows that no known methods are capable of transplanting purified ES cell-derived cardiomyocytes to remain engrafted while retaining their purity.

In addition, in order to prepare cell transplants that are intended for use in therapy on the human body, serum and other factors that are derived from other animals must be excluded. In the method of preparing cardiomyocytes to be used in transplantation, culture is usually performed in the presence of serum; but it is known that under serum-free conditions, human ES cells can form embryoid bodies, which contain cardiomyocytes in comparable amounts to those obtained by the usual culture in the presence of serum (Non-Patent Document 10: Stem cells and development 15: 931-941, 2006). However, no known reports including this report have described a ease of transplanting cardiomyocytes that were prepared without using factors such as serum that were derived from other animals.

Thus, in order that the cardiomyocytes could be successfully transplanted to the heart, several problems, such as the inclusion of cells other than cardiomyocytes, the low engraftment rate of transplanted cardiomyocytes and the inability to exclude components derived from other species, must be solved altogether.

Further, in connection with their transplantation to the cardiac tissue, it is contemplated to transplant cardiomyocytes in the form of so-called "cell sheets". As regards the preparation of cell sheets, it is known that neonatal cardiomyocytes are used to form a single layered sheet and up to three of such sheets can be stratified in vitro (Non-Patent Document 11: FASEB J. 2006 April; 20(6): 708-10). However, this document also states that, on account of limited oxygen permeability, the cell sheets cannot be made any thicker without neovascularization to the cell sheet, and it is not possible yet to prepare a desired cell sheet that fits the size of the diseased tissue of the heart.

As described above, the stated of the art is such that the preparation of cardiomyocytes to be used in transplantation and the transplantation of those cardiomyocytes need further improvements from the viewpoint of practical feasibility.

Patent Document 1: US 2005-0214938 A

Non-Patent Document 1: Zhonghua Yi Xue Za Zhi 2003, 83, 1818-22

Non-Patent Document 2: Circulation Research 2002, 90(3):e-40

Non-Patent Document 3: Circulation Research 2007 2, 100: 263-272

Non-Patent Document 4: Developmental Dynamics 235; 2200-2209, 2006

Non-Patent Document 5: Science 1994, 264(5155): 98-101

Non-Patent Document 6: Cardiovasc Res, 2007 May 17 (Flk1(+) cardiac stem/progenitor cells derived from embryonic stem cells improve cardiac function in a dilated cardiomyopathy mouse model)

Non-Patent Document 7: Stem Cells. 2007 May 31 (Differentiation in vivo of Cardiac Committed Human Embryonic Stem Cells in Post-Myocardial Infarcted Rats)

Non-Patent Document 8: FASEB J. 2007 Apr. 13 (Identification and selection of cardiomyocytes during human embryonic stem cell differentiation)

Non-Patent Document 9: J Exp Med. 2006 Oct. 2; 203 (10): 2315-27

Non-Patent Document 10: Stem Cell and Development 15: 931-941, 2006

Non-Patent Document 11: FASEB J. 2006 April; 20(6): 708-10

DISCLOSURE OF THE INVENTION

Problems to be Solved by the Invention

Hence, the present inventors studied the essential conditions that are assumed at least at present for clinical use of cultured cardiomyocytes and found, as a result, the following problems.

(1) Purification of cardiomyocytes: When cardiomyocytes are to be obtained from the living body or pluripotent stem cells, safety cannot be secured if they are contaminated by unknown cells, so in whichever case, it is essential that the cardiomyocytes be highly purified. In order to maintain the purity of such highly purified cardiomyocytes in a consistent manner, it would be necessary that the cardiomyocytes obtained from the living body or pluripotent stem cells be dispersed to discrete cells (as single cells), the individual cells being distinguished from one type to another so that only the cardiomyocytes can be selected.

(2) Origin of cardiomyocytes: Differences in the properties of cardiomyocytes that exist between species not only cause the problem of immune rejection and ethical problems but also present serious influences on clinical safety and efficacy, so it is important to use donor cells originating from the same species as the recipient individual.

(3) Exclusion of factors derived from animals of other species: To avoid immunogenicity and contamination by unknown pathogens, contaminants, such as serum, that are derived from animals of other species must be excluded.

(4) Engraftment of transplanted cardiomyocytes: Transplanted cardiomyocytes are required to function in the same manner as the cardiomyocytes in the host but, in the first place, they must be engrafted in the host cardiomyocytes (kept engrafted for an extended period of time).

(5) The cells must mature (grow to a bigger size) at the next stage.

In short the object of the present invention is to provide a means by which cardiomyocytes that have been purified to such an extent that they are free from non-cardiomyocytes and any components derived from other species can be transplanted with an improved engraftment rate that promotes maturation.

Means for Solving the Problems

In order to improve the engraftment rate of cardiomyocytes that were derived from the living body or pluripotent stem cells and which were purified to such an extent that they were free from non-cardiomyocytes and any components derived from other species, the present inventors studied the possibility of constructing cell masses from the purified cardiomyocytes. As a result, we revealed that the object stated above could be solved by providing a method of preparing cell masses of cardiomyocytes derived from pluripotent embryonic stem cells (ES cells) or induced pluripotent stem cells (iPS cells), characterized in that cell masses containing cardiomyocytes that had been differentiated and induced from ES cells or iPS cells were dispersed to single cells to thereby obtain purified cardiomyocytes, which were the cultured in a culture medium under serum-free conditions so that they were reaggregated.

The inventors of the present invention first used cardiomyocytes derived from the living body and studied the possibility of solving the above-stated object. To be more specific, using the cardiomyocytes derived from the living body that had been purified to such an extent that they were free from non-cardiomyocytes and any components derived from other species, the present inventors studied the possibility of enhancing the engraftment rate of such cardiomyocytes after transplantation.

As it turned out, the purified cardiomyocytes derived from the living body were not capable of forming cell masses even after the lapse of 24 hours culturing in a culture medium containing 10% serum. This result strongly suggested that the known method of forming cell masses of cardiomyocytes, as derived from the living body, that was effected in an unpurified state was strongly dependent on the auxiliary action of non-cardiomyocytes. In a further experimental study conducted to see how the purified cardiomyocytes derived from the living body would behave under serum-free conditions, those cells were unable to construct cell masses; on the contrary, they themselves underwent cell death. These results led to the conclusion that "constructing cell masses of unpurified cardiomyocytes derived from the heart in the living body" is an improbable technique and that it is even impossible to predict the behavior, in a serum-free condition, of purified cardiomyocytes derived from the heart in the living body.

Next, in the known methods of preparing cell masses of aggregated cardiomyocytes, cells derived from the heart in neonatal or fetal animals were used, which were cultured in a serum-containing culture medium. This is based on the common recognition that sera generally have a strong protective effect, irrespective of the cell species. However, as mentioned before, if therapy is performed on the human body, the use of factors derived from other animals (such as serum) must be avoided. Hence, using serum-free media that were supplemented with various additives containing serum substitutes rather than serum, the present inventors studied the aggregating ability of the cardiomyocytes derived from the living body. However, under any of the serum-free conditions tested, the cardiomyocytes derived from the living body were unable to construct the desired cell masses and their survival rate was also poor.

Given a report stating a known method that, when cardiomyocytes derived from the living body were cultured as cell masses, the survival of the cardiomyocytes was maintained for an extended period of time, the present inventors made an attempt to form cell masses of purified cardiomyocytes, as derived from the living body, under serum-free conditions. As it turned out, however, no cell masses could be formed even after five days of culture. This experimental result gave the new finding that, under serum-free conditions, the purified cardiomyocytes derived from the living body were not capable of constructing cell masses.

Hence, the present inventors speculated that it might be possible to overcome this technical difficulty by changing the source of supply of cardiomyocytes. As a result of making similar studies with various supply sources, the present inventors revealed that cardiomyocytes derived from purified embryonic stem cells bound together rapidly enough in only 12 hours even under serum-free conditions, whereby three-dimensional cell masses of cardiomyocytes could for constructed, and that they had already started to contract synchronously at that time.

This shows that cardiomyocytes derived from embryonic stem cells were capable of efficient construction of cell adhesion between purified cardiomyocytes and it also shows that the purified cardiomyocytes derived from embryonic stem cells have high ability to aggregate under serum-free conditions. Since this finding was reproduced with more than one species using embryonic stem cells derived from the respective species, the feature described above would be a nature that is common to the cardiomyocytes obtained from human and otherwise derived embryonic stem cells. Based on the nature specific for this embryonic stem cell under serum-free conditions, the present inventors successfully formed cell masses of purified cardiomyocytes under serum-free conditions for the first time in the art.

Further, it was predicted from a known report that embryonic stem cell-derived cardiomyocytes having low engraftment rate alter transplantation would also have low capacity to reaggregate (Transplantation 70: 1310-1317, 2000); on the other hand, it had been predicted that the very attempt to aggregate the purified cardiomyocytes derived from embryonic stem cells would be difficult to realize, making one believe that they could not be aggregated. Nevertheless, contrary to this prediction, the present inventors showed for the first time in the art that the purified cardiomyocytes derived from embryonic stem cells could construct cell masses without the aid of other cells and that a significant improvement in cell engraftment rate could be achieved by using the constructed cell masses in transplantation. Briefly, the present inventors successfully found out that the cardiomyocytes derived from embryonic stem cells had entirely different characteristics from the cardiomyocytes derived from the heart in the living body in that they could be purified to single cells and that they could construct cell masses even under serum-free conditions.

Furthermore, with a view to finding out a method by which cell masses more suitable for transplantation could be prepared from the cardiomyocytes derived from embryonic stem cells, the present inventors studied additives that might be added to culture media as a means by which the cardiomyocytes derived from embryonic stem cells could construct cell masses more efficiently under serum-free conditions. As a result, when insulin, transferrin and selenium (ITS) were added as the additives, the cell masses showed a stronger spontaneous pulsation than the cell masses to which no ITS had been added and this phenomenon was observed with good reproducibility. Briefly, the addition of ITS (in particular, insulin) was shown to be desirable for constructing cell masses using the purified cardiomyocytes derived from embryonic stem cells. Note that insulin is the most important factor among ITS, with transferrin and selenium playing an auxiliary role.

In the next place, the present inventors added ITS to a serum-free basal culture medium (hereinafter referred to as the basal culture medium) and further added a basic fibroblast growth factor (bFGF) and/or an insulin-like growth factor 1 (IGF1) to the basal culture medium; as it turned out, when bFGF alone was added, the cell masses at day 5 after their formation had a significant increase in diameter, indicating that the cells of interest were protected. This phenomenon was not observed under the serum-containing culture conditions and it was cell protecting and proliferating effects that were characteristic of the serum-free conditions under which bFGF alone was added. It was known that bFGF had a cell protecting action, a cell growth promoting action and the like on cardiomyocytes being cultured under such experimental conditions that plane culture was performed in the presence of supplemented serum (J Mol Cell Cardiol. 2007 January: 42(1): 222-33; and Cardiovasc Res. 2004; 64: 516-25), but it was entirely unknown that prolonged growth and protection of cardiomyocytes should occur under serum-free conditions.

This effect was greater than what was observed when cell masses were formed using a culture medium supplemented with 10% serum; on the other hand, in the case where bFGF was added but cell masses were not formed by plane culture, the effect of interest was smaller than what was observed when cell masses were formed using the culture medium supplemented with 10% serum. From the results of these two experiments, it was assumed that, in order to ensure that bFGF would produce the cell protecting and growth promoting effects in excess of those obtained by forming cell masses using the culture medium supplemented with 10%) serum, it was essential to construct the cell masses.

Hence, in order to confirm whether the construction of cell masses was an essential condition for those effects to be displayed, the present inventors performed plane adhesive culture of cardiomyocytes derived from purified mouse embryonic stem cells, with bFGF added to the culture medium, and analyzed the effects of the added bFGF.

In plane culture where no cell masses formed, the purified cardiomyocytes could hardly survive in such an environment that ITS was added to the basal culture medium. However, upon addition of bFGF, more cells were found to survive and adhered to the culture plate. This action was smaller than the effect that was observed when cell masses were formed using the culture medium supplemented with 10% serum.

In the case of constructing cell masses of purified cardiomyocytes derived from embryonic stem cells, the action of condition of serum-free+ITS+bFGF was compared with the action of 10% serum after long-time culture; in the 10% serum-containing culture medium, the size of cell masses decreased significantly whereas it increased significantly in the serum-free+ITS+bFGF group. This indicated that the action of bFGF as discovered by the present inventors was the synergistic effect of all three elements, purification, serum-free, and cell masses.

From this result, the present inventors found that the addition of ITS and/or bFGF to the serum-free culture medium allowed the cell masses of cardiomyocytes to maintain their state for an extended period of time. By virtue of this finding, the survival rate of cardiomyocytes could be increased to 90% or more, an outstanding improvement over the 60-70% value for the conventional plane culture method.

Before the accomplishment of the present invention, cell masses of cardiomyocytes could not be constructed under serum-free and high-purity conditions; however, on the basis of the foregoing, the present inventors overcame this difficulty by using cardiomyocytes derived from embryonic stem cells; we also found that cell masses of cardiomyocytes could be constructed most efficiently in the presence of added ITS and bFGF.

Thus, in one of the embodiments, the present invention also provides a method of preparing cell masses of cardiomyocytes derived from embryonic stem cells, characterized in that purified cardiomyocytes derived from embryonic stem cell obtained by dispersing aggregated cell masses that contain cardiomyocytes differentiated and induced from embryonic stem cells to single cells are cultured in a culture medium under serum-free conditions so that they are reaggregated. The culture medium to be used for the culture described above desirably supplemented with at least insulin among ITS, and in a more desirable embodiment, bFGF may also be supplemented, in the method described above, cell masses dispersed to single cells need not to be cultured in a single space as in the known methods but they may be divided into 10,000 cell groups at maximum and cultured in a corresponding number of independent spaces.

If contaminated by proliferative non-cardiomyocytes, cell masses of aggregated cells will grow to an extremely large size and also change in morphology. In addition to this index, staining with a fluorescence dye that accumulates in mitochondria may be used to identify the proliferative cells as ones in which the dye finds difficulty accumulating. Cell masses contaminated by such non-cardiomyocytes may be rejected from use in transplantation therapy or the like so as to ensure that the slightest contamination by proliferative non-cardiomyocytes is excluded from implanted cells.

In addition, it was previously reported that purified cardiomyocytes derived from embryonic stem cell as dispersed to disaggregated cells (single cells) were not engrafted if transplanted as such to the cardiac tissue in an individual (the living body) and the present inventors obtained the same result. In the prior art, this problem was solved by mixing the purified cardiomyocytes derived from embryonic stem cell with auxiliary cells, clearly showing that the protective action of non-cardiomyocytes in the living body is essential to the survival of cardiomyocytes. However, contamination of non-cardiomyocytes can potentially cause serious unpredictable side effects that might threaten the life of a patient after transplantation, so the present inventors speculated that greater safety and a higher therapeutic effect would be secured if the purified cardiomyocytes could be transplanted into an individual (the living body) without mixing them with auxiliary cells but keeping them at high purity.

Hence, the present inventors got the idea of exploiting the cell masses of purified cardiomyocytes derived from embryonic stem cell obtained by the method described above and found that by transplanting those cell masses to the cardiac tissue of an individual (the living body), the engraftment rate after transplantation could be significantly improved. In other words, the present inventors found that, when the purified cardiomyocytes derived from embryonic stem cell obtained by dispersing cell masses to single cells were cultured in a culture medium under serum-free conditions so that they were reaggregated to form cell masses, the engraftment rate of the purified cardiomyocytes derived from embryonic stem cell after transplantation could be significantly improved.

Hence, another embodiment of the present invention relates to a method of treating cardiac disease, characterized in that cell masses obtained by reaggregating cardiomyocytes that are derived from embryonic stem cells and which have been purified by dispersing to single cells are transplanted to the cardiac tissue (especially, a diseased part of the cardiac tissue) in an individual (the living body) such that they are engrafted. The term "engraftment" as used herein means surviving within the host organ and remaining adherent in it for an extended period of time.

Further, as described above, there was known a method that allowed up to three mono-layered sheets of neonatal cardiomyocytes to be stratified but no thicker sheets of cardiomyocytes could be prepared.

To solve this problem, the present inventors got the idea of exploiting the cell masses of purified cardiomyocytes derived from embryonic stem cell obtained by the method described above. The cell masses of interest were constructed by the method described above and the obtained cell masses were recovered and seeded on the surface of a wall-partitioned, non-cell-adhering vessel with no space between cell masses such that adjacent cell masses would be continuously in contact with each other, followed by suspension culture. As a result, the cell masses were conjugated together over time to form a sheet of cell masses of cardiomyocytes in a thickness of 50-300 μm; it was thus found that a so-called "cell sheet" having a greater thickness than the limit of the prior art could be prepared outside the living body. Thus, it became clear that in actual modes of application, a desired number of cell masses in a desired size of purified cardiomyocytes derived from embryonic stem cells could be used to prepare a cell sheet of a desired size.

Hence, a further embodiment of the present invention relates to a method of preparing a sheet of cell masses of cardiomyocytes (cell sheet), characterized in that cell masses of purified cardiomyocytes derived from embryonic stem cells are subjected to suspension culture as they are placed at close intervals in the same plane and that the suspension culture is performed until the cell masses are conjugated together to have a desired thickness between 50 and 300 μm.

The present invention has revealed that the cell masses of purified cardiomyocytes derived from embryonic stem cell having the features described above can be transplanted to the cardiac tissue such that they are engrafted. These cell masses can be used as a medical device for transplantation that can be transplanted into animal bodies including the human body.

Hence, in a further embodiment of the present invention, there is provided a medical device comprising cell masses of cardiomyocytes derived from embryonic stem cell that have been prepared by a method which comprises preparing cell masses of aggregated cells that contain cardiomyocytes differentiated and induced from embryonic stem cells, dispersing the cell masses to single cells to thereby yield purified cardiomyocytes derived from embryonic stem cell, and culturing the cardiomyocytes in a culture medium under serum-free conditions so that they are reaggregated. This medical device is intended for use in transplantation such that it is transplanted to the cardiac tissue of an individual such that it is engrafted; it exhibits a significant effect in that it can be applied to a patient who needs cardiac transplantation.

Thus, the present inventors made intensive studies on culture conditions that would allow for a significant improvement in the survival rate of cardiomyocytes derived from embryonic stem cell that had been dispersed to disaggregated cells (single cells) to become completely purified; as a result, we found that the cardiomyocytes had such a new characteristic that they aggregated to form cell masses when they were cultured in a culture medium under conditions containing no animal-derived serum (i.e., serum-free conditions), preferably in the culture medium containing insulin, more preferably in the culture medium containing transferrin, selenium, and/or a basic fibroblast growth factor in addition to insulin. The present inventors transplanted those cells to the cardiac tissue of an individual (living body) and obtained a new finding that their engraftment rate in the tissue was significantly improved. The present inventors obtained another new finding that, using those cells, we could obtain a sheet of cell masses of cardiomyocytes having a greater thickness than those expected from the known technique, as well as a medical device comprising those cell masses; these findings led to the accomplishment of the present invention.

Those findings were obtained by culturing embryonic stem cells and similar findings can also be obtained by using other pluripotent stem cells instead of the embryonic stem cells. To state more specifically, when pluripotent stem cells that had been dispersed to a suspension of disaggregated cells (single cells) to become completely purified were cultured in a culture medium under conditions containing no animal-derived serum (i.e., serum-free conditions), preferably in the culture medium containing insulin, more preferably in the culture medium containing transferrin, selenium, and/or a basic fibroblast growth factor in addition to insulin, those cells were able to aggregate to form cell masses, and the survival rate of cardiomyocytes could be improved considerably. The pluripotent stem cells that can be used include not only embryonic stem cells but also all other pluripotent stem cells having traits similar to those of embryonic stem cells, as derived from the cells in adult organs and tissues in mammals, as well as their bone marrow cells, blood cells, and even embryonic and fetal cells; examples are embryonic germ cells (EG cells), germline stem cells (GS cells), and induced pluripotent stem cells (iPS cells).

Thus, the present invention relates to the following matters.

(1) A method of preparing cell masses of cardiomyocytes derived from pluripotent stem cells, characterized in that purified cardiomyocytes derived from pluripotent stem cell obtained by dispersing aggregated cell masses that contain cardiomyocytes differentiated and induced from pluripotent stem cells (such as embryonic stem cells, embryonic germ cells, germline stem cells or induced pluripotent stem cells) to single cells are cultured in a culture medium under serum-free conditions so that they are reaggregated.

(2) The method according to (1) above, wherein the culture medium contains insulin.

(3) The method according to (1) or (2) above, wherein the culture medium contains at least one substance selected from the group consisting of transferrin, selenium, a basic fibroblast growth factor (bFGF), an epidermal growth factor (EGF), a platelet-derived growth factor-BB (PDGF-BB), and endothelin-1 (ET-1).

(4) The method according to any one of (1) to (3) above, wherein the content in the culture medium is 0.1 to 10 mg/L of insulin, 0.1 to 10 μg/L of transferrin, 0.1 to 10 μg/L of selenium, 1 ng/ml to 100 ng/ml of the basic fibroblast growth factor, 1 ng/ml to 1000 ng/ml of the epidermal cell growth factor, 1 ng/ml to 1000 ng/ml of the platelet-derived growth factor, and $1\times10^{-8}$ to $1\times10^{-6}$ M of endothelin-1 (ET-1).

(5) A method of treating cardiac disease, characterized in that cell masses obtained by reaggregating cardiomyocytes that are derived from purified pluripotent stem cells dispersed to single cells are transplanted to the cardiac tissue of an individual such that they are engrafted.

(6) The method according to (5) above, wherein the cell masses of cardiomyocytes are those that are obtained by the method according to any one of (1) to (4) above.

(7) The method according to (5) or (6) above, wherein the transplantation comprises injecting the cell masses of cardiomyocytes into the cardiac tissue.

(8) The method according to (5) or (6) above, wherein the transplantation comprises transplanting a sheet of cell masses of cardiomyocytes onto the cardiac tissue.

(9) A method of preparing a sheet of cell masses of cardiomyocytes, characterized in that cell masses of purified cardiomyocytes derived from pluripotent stem cells are seeded on the surface of a wall-partitioned, non-cell-adhering vessel, with no space between cell masses such that adjacent cell masses will be continuously in contact with each other, followed by suspension culture which is maintained until the cell masses are conjugated together to have a desired thickness of 50-300 μm.

(10) The method according to (9) above, wherein the cell masses of cardiomyocytes are those obtained by the method according to any one of (1) to (4) above.

(11) A medical device comprising cell masses of cardiomyocytes derived from pluripotent stem cell for use in transplantation to the cardiac tissue of an individual such that they are engrafted, wherein the medical device is prepared by a method comprising preparing cell masses of aggregated cells that contain cardiomyocytes differentiated and induced from pluripotent stem cells, dispersing the cell masses to single cells to thereby yield purified cardiomyocytes derived from pluripotent stem cell, and culturing the cardiomyocytes in a culture medium under serum-free conditions so that they are reaggregated.

(12) The medical device according to (11) above, wherein the transplantation comprises injecting the cell masses of cardiomyocytes into the cardiac tissue.

(13) The medical device according to (11) above, wherein the transplantation comprises transplanting a sheet of cell masses of cardiomyocytes onto the cardiac tissue.

Advantages of the Invention

Discovered by the present invention is a characteristic which describes that cardiomyocytes derived from pluripotent stem cell that have been purified by dispersing to single cells have the ability to reaggregate when they are cultured under serum-free conditions. By constructing cell masses by the method of the present invention, the cardiomyocytes of interest can be cultured for an extended period of time with their survival rate or growth capacity being maintained at high level. In addition, when those cardiomyocytes were transplanted to the cardiac tissue of an individual (the living body), their engraftment rate in the tissue was found to significantly increase and they remained engrafted within the cardiac tissue for an extended period without mingling with other cells. This technique has given feasibility to a treatment method that holds promise in cell therapy, and a medical device that comprises cell masses of cardiomyocytes.

BRIEF DESCRIPTION OF THE DRAWINGS

FIGS. 2A and 2B show the construction of cell masses of cardiomyocytes using purified cardiomyocytes derived from marmoset embryonic stem cells, either 24 hours (FIG. 2A) or 48 hours (FIG. 2B) after dispensation.

FIG. 7B: 6 days).

FIGS. 9A, 9B, 9C, and 9D show the results of measuring the viability of cells in tissue of purified, single-cell cardiomyocytes derived from mouse embryonic stem cells after they were transplanted to the heart without applying the reaggregation method but as they remained as dispersed cells.

FIGS. 10A, 10B, and 10C show that, when purified cardiomyocytes derived from mouse embryonic stem cells as formed into cell masses by the reaggregation method were labeled with a red dye (Mitotracker Red) and transplanted to the heart, the cardiomyocytes survived efficiently, Following transplantation, the heart was fixed and stained with an anti-sacroplasmic actinin antibody, as shown in FIG. 10A. Staining with Mitotracker Red is depicted in FIG. 10B. A merging of the two staining patterns is depicted in FIG. 10C.

FIGS. 11A and 11B show the result of analyzing the survival rate of the cells in the cardiac tissue by measuring the cell count in the cardiac tissue, and FIGS. 11C and 11D show that the cell masses of mouse cardiomyocytes remained engrafted in the host heart for a prolonged period and could mature with the lapse of time.

FIG. 19A shows the result of an FACS analysis conducted with the mitochondrial indicator TMRM. FIG. 19B shows the result of immunostaining (with actinin and Nkx2.5) of purified cardiomyocytes that have been subjected to adhesive culture. FIG. 19C shows the appearance of the purified cardiomyocytes 24 hours after they were seeded in a non-cell-adhesive 96-well culture dish.

BEST MODE FOR CARRYING OUT THE INVENTION

Figure 1:
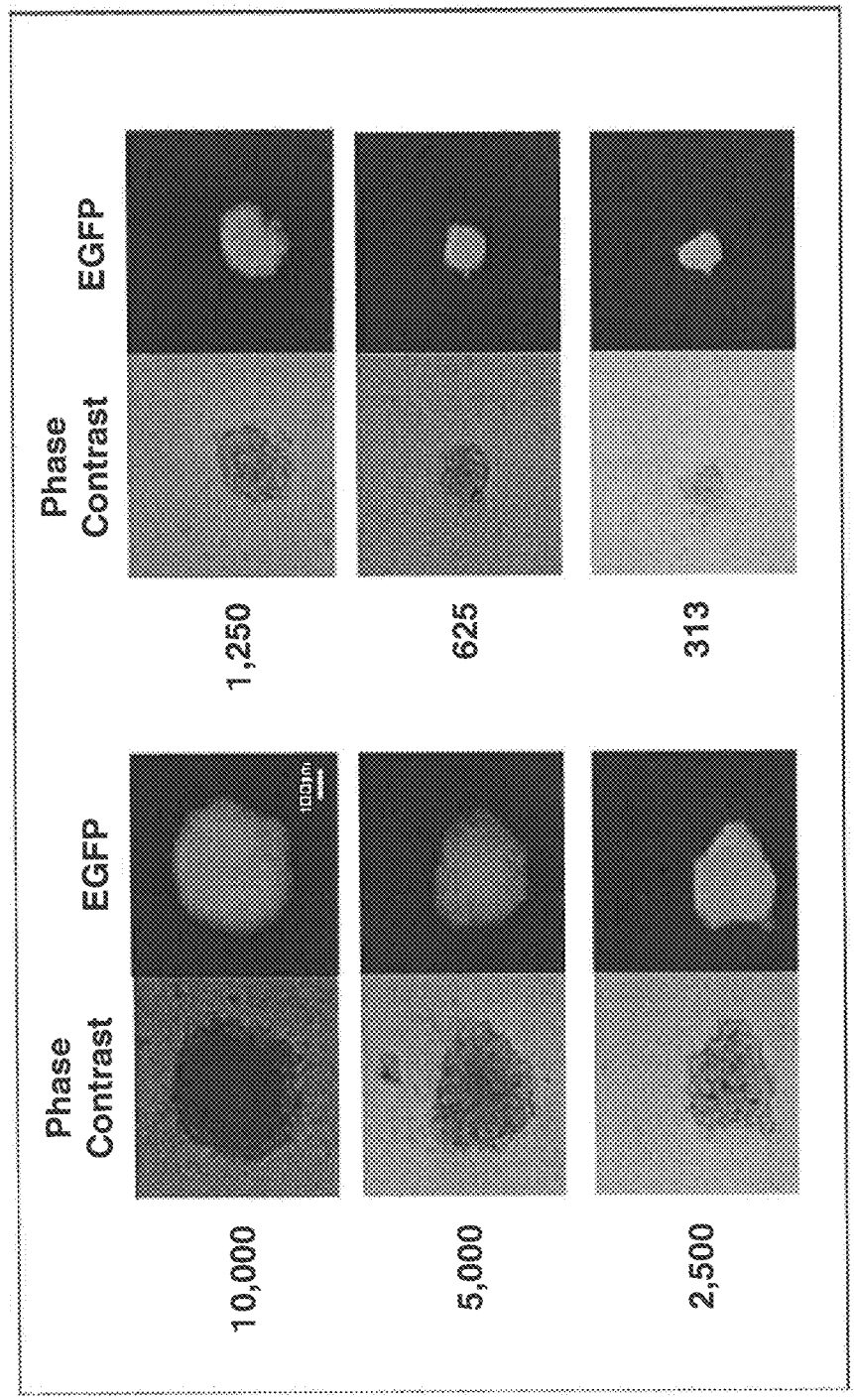
FIG. 1 shows a method of constructing cell masses of cardiomyocytes using purified cardiomyocytes derived from enhanced green fluorescent protein (EGFP) expressing mouse embryonic stem cells, and cell masses obtained by using from 313 to 10000 purified cardiomyocytes derived from the mouse embryonic stem cells.

Those ordinarily skilled in the art who, in order to carry out the present invention, needs to know about methods in molecular biology, genetic engineering methods such as recombinant DNA technology, general methods in cell biology as well as the prior art may, unless otherwise instructed, refer to standard books in those fields, Examples of such books include: "Molecular Cloning: A Laboratory Manual, $3^{rd}$ Edition" (Sambrook & Russell, Cold Spring Harbor Laboratory Press, 2001); "Current Protocols in Molecular biology" (Ed. by Ausubel et al. John Wiley & Sons, 1987); "Methods In Enzymology in series" (Academic Press); "PCR Protocols: Methods in Molecular Biology" (Ed. by Bartlett & Striling, Humana Press, 2003); "Animal Cell Culture: A Practical Approach, 3rd Edition" (Ed. by Masters, Oxford University Press, 2000); and "Antibodies: A Laboratory Manual" (Ed. by Harlow et al, & Lane, Cold Spring Harbor Laboratory Press, 1987). The reagents and kits for use in cell culture and experiments in cell biology that are referred to herein are available from commercial suppliers such as Sigma, Aldrich, Invitrogen/GIBCO, Clontech, and Stratagene.

(1) Pluripotent Stem Cells

Those ordinarily skilled in the art who, in order to carry out the present invention, needs to know about cell culture using pluripotent stem cells and general methods for experiments in developmental and cell biology may, unless otherwise instructed, refer to standard books in those fields. Examples of such books include: "Guide to Techniques in Mouse Development" (Ed. by Wasserman et al., Academic Press, 1993); "Embryonic Stem Cell Differentiation in vitro" (M. V. Wiles, Meth. Enzymol. 225: 900, 1993); "Manipulating the Mouse Embryo: A laboratory manual" (Ed. by Hogan et al., Cold Spring Harbor Laboratory Press, 1994); "Embryonic Stem Cells" (Ed. by Turksen, Humana Press, 2002). The reagents and kits for use in cell culture and experiments in developmental and cell biology that are referred to herein are available from commercial suppliers such as Invitrogen/GIBCO and Sigma.

For the methods of preparing, serially culturing and preserving mouse or human pluripotent stem cells, standard protocols have already been established and those ordinarily skilled in the art who wants to carry out the present invention are able to use those pluripotent stem cells by referring to a plurality of reference documents and the like in addition to the reference books listed in the preceding sections. Such documents include the following: Matsui et al, Cell 70: 841, 1992; Thomson et ah, U.S. Pat. No. 5,843,780; Thomson et al. Science 282: 114, 1998; Shamblott et al, Proc. Natl. Acad. Sci. USA 95: 13726, 1998; Shamblott et al., U.S. Pat. No. 6,090,622; Reubinoff et al., Nat. Biotech. 18: 399, 2000; and International Publication WO 00/27995 A1. For other animal species, such as monkey (Thomson et al., U.S. Pat. No. 5,843,780; and Proc, Natl. Acad. Sci. USA, 92, 7844, 1996), rat (Iannaccone et al., Dev. Biol. 163: 288, 1994; and Loring et al., International Publication WO 99/27076 A1), chicken (Pain et al., Development 122: 2339, 1996; U.S. Pat. Nos. 5,340,740; and 5,656,479), and swine (Wheeler et al., Reprod, Fertil. Dev. 6: 563, 1994; and Shim et al., Biol. Reprod. 57: 1089, 1997), methods are known that can establish pluripotent cells such as embryonic stem cells and embryonic stem cell-like cells, and those pluripotent stem cells that can be used in the present invention may be prepared or used in accordance with the methods described in those documents.

The method of the present invention can be applied to pluripotent stem cells derived from any mammals. For example, it may be applied to pluripotent stem cells derived from the mouse, bovine, goat, dog, eat, marmoset, rhesus monkey, and human; however, it is not limited to the pluripotent stem cells derived from these animal species. The pluripotent stem cells to be used in the present invention may be exemplified by embryonic stem cells (ES cells) derived from mammals such as mouse, monkey and human that are already widely used as cultured cells.

Specific examples of mouse-derived embryonic stem cells include EB3 cell, E14 cell, D3 cell, CCE cell, R1 cell, 129SV cell and J1 cell. The mouse-derived embryonic stem cells according to the present invention are available from the American Type Culture Collection (ATCC), Chemicon, Cell & Molecular Technologies, etc.

As for the Monkey-derived embryonic stem cells, those cell lines established from rhesus monkey (*Macaca mulatta*) (Thomson et al, Proc. Natl Acad. Sci. USA 1995; 92: 7844), cynomolgus monkey (*Macaca fascicularis*) (Suemori et al., Dev. Dyn. 2001; 222: 273-279) and common marmoset (*Callithrix jacchus*) (Sasaki et al., Stem Cells. 2005; 23: 1304-1313) have been reported and are available. For example, marmoset embryonic stem cells are also available from the Central Institute for Experimental Animals (a judicial foundation).

As of today, more than several tens of human derived embryonic stem cell lines have been established in the world; for example, in the list at the US National Institutes of Health (http://stemcells.nih.gov/registry/index.asp), numerous cell lines are registered for public use, and other cell lines are available from the commercial sources including Cellartis, ES Cell International, Wisconsin Alumni Research Foundation, etc. In Japan, human derived embryonic stem cell lines are also available from the Stem Cell Research Center, adjunct facilities to the Institute for Frontier Medical Sciences, Kyoto University (national university corporation) (Suemori et al., Biochem. Biophys. Res. Commun., 2006; 345: 926-932).

It was also reported that embryonic stem cell lines have been established for bovine (Mitalipova et ah, Cloning 2001; 3: 59-67), avian (Petitte et al., Mech. Dev. 2004; 121; 1159-1168), and zebrafish (Fishman, M. C., Science 2001; 294: 1290-1291).

While embryonic stem cell lines are generally established by culturing early embryos, they can also be prepared from early embryos into which the nuclei of somatic cells have been transferred (Munsie et al., Curr. Biol. 10: 989, 2000; Wakayama et al., Science 292: 740, 2001; and Hwang et al., Science 303: 1669, 2004). There have also been reported an attempt to develop parthenogenetic embryos to a stage comparable to the blastocyte stage and to prepare embryonic stem cells from that stage (U.S. patent publication Ser. No. 02/168,763 A1; and Vrana K et al., Proc. Natl. Acad. Sci. USA 100: 11911-6) and a method in which an embryonic stem cell is fused to a somatic cell to make an embryonic stem cell carrying the genetic information from the somatic cell nucleus (International Publication WO 00/49137 A1; and Tada et al., Curr. Biol. 11: 1553, 2001). The embryonic stem cells that can be used in the present invention also include those that have been prepared by the methods described above, as well as those in which the genes located on their chromosomes have been modified by genetic engineering techniques.

The pluripotent stem cells that can be used in the method according to the present invention are not limited to embryonic stem cells but include all other pluripotent stem cells having traits similar to those of embryonic stem cells, as derived from the cells in adult organs and tissues in mammals, as well as their bone marrow cells, blood cells, and even embryonic and fetal cells, in this case, the "traits similar to those of embryonic stem cells" may be defined by cellular biological properties that are specific to embryonic stem cells, as exemplified by the presence of a surface (antigen) marker specific to embryonic stem cells, expression of a gene specific to embryonic stem cells, as well as a teratoma forming capacity and chimeric mouse forming capacity. Specific examples of other applicable pluripotent stem cells include embryonic germ cells (EG cells) prepared from primordial germ cells, germline stem cells (GS cells) prepared from germ cells in the testis, and induced pluripotent stem cells (iPS cells) prepared from somatic cells such as fibroblasts by a special gene manipulation. Examples of the induced pluripotent stem cells include those that can be prepared by introducing specific factors into somatic cells and they can be prepared by the methods descried in a paper written by the research group of Professor Shinya Yamanaka at Kyoto University (K. Takahashi, et ah, "Induction of Pluripotent Stem Cells from Adult Human Fibroblasts by Defined Factors" Celt 2007 131: 861-872) and a paper written by Thomson's research group at Wisconsin University (J. Yu, et al., "induced Pluripotent Stem Cell Lines Derived from Human Somatic Cells" Science 2007 318: 1917-1920). Specifically, at least one gene selected from genes of Oct3/4, Sox2, e-Myc, Klf4, Nanog and LIN28 is transferred into a given somatic cell, the expression of any gene or protein that is specific for pluripotent stem cells is detected, and those cells that express such gene or protein are selected as pluripotent stem cells. Like embryonic stem cells, the induced pluripotent stem cells thus prepared can be cultured together with a basic fibroblast growth factor in the presence of mouse fibroblasts deactivated for growth or cells that can be substituted for them, and the cultured cells can be used as pluripotent stem cells, similar to embryonic stem cells.

It has heretofore been revealed that the induced pluripotent stem cells described above have the same properties as the embryonic stem cells with regard to the characteristics of differentiation into various tissues and those of gene expression within cells (Park I. H. et al., Nature, 2008, 451, 141-147) and the conditions for inducing differentiation of embryonic stem cells into a variety of tissues can directly be applied to the induced pluripotent stem cells (Takahashi and Yamanaka, Saibou Kogaku (Cell Engineering), Vol. 27, No. 3, 252-253, 2008).

(2) Methods of Inducing Differentiation of Pluripotent Stem Cells into Cardiomyocytes The following description relates to embryonic stem cells (ES cells) as an example of pluripotent stem cells. When embryonic stem cells capable of differentiating into cardiomyocytes are subjected to an appropriate treatment for inducing differentiation into cardiomyocytes, they start to differentiate into cardiomyocytes. For example, differentiation of mouse embryonic stem cells into cardiomyocytes can be induced by the hanging drop method, in which the embryonic stem cells are subjected to suspension-culture in a culture media free of a leukemia-inhibiting factor (LIP) until cell masses (embryoid bodies) are formed. Alternatively, marmoset embryonic stem cells or human embryonic stem cells may likewise be subjected to a treatment for inducing differentiation into cardiomyocytes. To induce differentiation of embryonic stem cells into cardiomyocytes, any known methods may be employed. For example, a method of inducing differentiation in the presence of a substance that suppresses BMP signaling (WO2005/033298) and a method of inducing differentiation in the presence of a substance that stimulates activation of the canonical Wnt signaling pathway (PCT/JP2007/59242, published as WO2007/126077).

(3) Purification of Cardiomyocytes

After inducing the differentiation of embryonic stem cells into cardiomyocytes by the method described in (2) above, the cardiomyocytes may be purified (selected) by any method that is capable of dispersing cardiomyocytes into disaggregated cell (single cells) and purifying them as individual cardiomyocytes. For example, a method of selection using mitochondria in cardiomyocytes as an index (WO2006/022377) and a method of selecting cells that can survive under low nutrient conditions (PCT/JP2007/051563, published as WO2007/088874) may be used to purify (select) only cardiomyocytes.

(4) Preparing Cell Masses of Cardiomyocytes

The purified cardiomyocytes derived from embryonic stem cell that have been obtained through dispersing to single cells according to the method described in (3) above may be cultured under serum-free conditions such that they are aggregated to prepare cell masses of cardiomyocytes derived from embryonic stem cells. Preferably, the culture medium used for this culture contains at least one substance selected from the group consisting of insulin (0.1 to 10 mg/L), transferrin (0.1 to 10 µg), selenium (0.1 to 10 µg/L), a basic fibroblast growth factor (bFGF: 1 ng/ml to 100 ng/ml), an epidermal cell growth factor (1 ng/ml to 1000 ng/ml), a platelet-derived growth factor (1 ng/ml to 1000 ng/ml), and endothelin-1 (ET-1) ($1 \times 10^{-8}$ to $1 \times 10^{-6}$ M).

The cell masses of purified cardiomyocytes derived from embryonic stem cell that have been obtained by the method described above contain proliferative cells as a small number of contaminant: if such proliferative cells are excluded from cells for transplantation, further safety can be secured. Currently known methods for purifying cardiomyocytes involve preliminary introduction of certain marker genes into the genome of the stem cells (FASEB J. 2000; 14: 2540-2548). All of these methods can provide 99% purity but they are incapable of guaranteeing 100±0% purity. For example, if $10^{11}$ cardiomyocytes are required for treating human myocardial infarction, 99% purity means contamination by $10^9$ non-cardiomyocytes. Thus, even a method that may be described as an almost perfect means of purification in light of the known state of the art does not enable 100% purification of cardiomyocytes and must be combined with further methods of purification or applied by other methods that guarantee safety.

Hence, the present inventors replicated the above-described method after intentionally mixing the cell masses of undifferentiated cardiomyocytes with embryonic stem cells. As it turned out, the undifferentiated embryonic stem cells which were more capable of growth than cardiomyocytes constructed separate larger cell masses outside the cell masses of cardiomyocytes. The cell masses of cardiomyocytes contaminated by the undifferentiated embryonic stem cells can be clearly detected by checking the overall sizes of the cell masses. The present inventors also added a mitochondrial indicator (e.g., TMRM) to the cell masses of interest, whereupon the cardiomyocytes that were rich in mitochondria were found bright whereas the embryonic stem cells and other proliferative cells that were not rich in mitochondria were found dark. Exclusion of the cell masses having the greater difference in fluorescence can be excluded automatically by making use of Arrayscan (Cellomics), Incell 1000 (GE/Amersham Biosciences, Cardiff, UK), Scanalyzer (Scanalyzer LemnaTec, Aachen Germany, "ImageXpress MICRO" (Molecular Devices, Union City, USA), "Pathway HT" (Becton Dickinson Biosciences), "Scan^R" (Olympus Soft Imaging Solutions, Germany), etc. Thus, the method described above provides a simple and automatic way to identify the contamination by the undifferentiated embryonic stem cells. Briefly, the proliferative cells that slightly mix with the purified cardiomyocytes derived from embryonic stem cell that have formed as aggregates into cell masses under serum-free culture conditions can be identified using the size and shape of such cell masses as indices, which is optionally combined with staining with a mitochondrial indicator and subsequent identification using fluorescence intensity and its distribution within cell masses as indices. In this way, the cell masses contaminated by non-cardiomyocytes can be excluded from the cells for transplantation to thereby achieve greater safety.

(5) Transplantation of Cell Masses of Cardiomyocytes to the Cardiac Tissue and Their Engraftment Using the cell masses obtained through aggregation by the method described above, namely, the cell masses of purified cardiomyocytes derived from embryonic stem cells, one can transplant only the cardiomyocytes to the cardiac tissue of an individual (the living body). For example, the cardiomyocytes may be directly injected into the cardiac tissue through a syringe; in this case, injection is feasible using a thin (29- or 30-gage), hence, less invasive needle. The engraftment rate of the cardiomyocytes transplanted by the method described above is significantly improved over the known methods. The term "engraftment" means that the transplanted cells survive within the host organ and remain adherent inside the organ for an extended period of time.

(6) Sheets for Transplantation Made of Cell Masses of Cardiomyocytes

By means of known methods, a sheet of cardiomyocytes thicker than three cells thick cannot be prepared at a time even if neonatal cardiomyocytes are used. However, in the present invention, after constructing cell masses of purified cardiomyocytes derived from embryonic stem cells, the obtained cell masses are recovered, seeded on the surface of a wall-partitioned, non-cell-adhering vessel with no space between cell masses such that adjacent cell masses will be continuously in contact with each other, and subjected to suspension culture, whereupon, the cell masses of cardiomyocytes are conjugated together over time to form a sheet of cell masses of cardiomyocytes (cell sheet) having a thickness of 50-300 µm. Hence, culture is performed until a desired thickness is formed. As a result, in actual application modes, cell masses in a desired size of purified cardiomyocytes derived from embryonic stem cells can be used in a desired number to prepare a cell sheet of a desired size.

EXAMPLES

The present invention is illustrated in greater detail by reference to the following examples.

Example 1: Preparation of Cardiomyocytes Derived from Mouse Embryonic Stem Cells and Purification of the Cardiomyocytes Using the Mitochondria Method The purposes of this Example were to prepare cardiomyocytes from mouse embryonic stem cells and to study whether it was possible to purify the prepared cardiomyocytes using a mitochondrial indicator.

As embryonic stem cells, EB3 cell line (Niwa H, et al., Nat Genet 2000; 24: 372-376) was used. An EGFP expressing unit was introduced into the EB3 cell line via a plasmid and EGFP expressing cells were acquired and established as a cell line. The thus acquired EGFP-expressing embryonic stem cells (EB3 cells) were suspended in an α-MEM culture medium (Sigma) such that the concentration of embryonic stem cells reached 75 cells/35 µL; the α-MEM culture medium was supplemented with heat-inactivated fetal bovine serum (55° C.×30 min) to a final concentration of 10%. Subsequently, the suspension of mouse embryonic stem cells thus prepared was distributed in a commercial cell culture 384-well plate (product of Greiner, Model 788161; i.d, of each well opening, 3.0 mm) and embryoid bodies were prepared in accordance with the following method.

The 384-well plate had a nominal allowable liquid volume of 25 µL per well but in order to raise the liquid level above the well openings by the effect of surface tension, the suspension was distributed in a volume of 35 µL per well. As a result, 75 embryonic stem cells were distributed per well. In this case, the suspension had to be supplied in a volume of 28 µL in order to reach the horizontal level in each opening and in an additional volume of 7 µL to rise above that horizontal level. For distribution of the suspension, a multi-channel pipette of Theremo Labsystems (Lot No. 4610070) or a distributing machine of BioTech Co., Ltd. (Model LD-01) was used.

The plate in which the culture medium containing the embryonic stem cells was distributed until it raised above the well openings was inverted upside down so that the culture medium was projecting downward from the lower edges of the well openings. As it was kept in this state, the plate was covered with a lid and culture was performed in an incubator at 37° C. in a 5% $CO_2$ atmosphere until embryonic stem cells grew in the projections from the lower edges of the well openings. One day after the start of culture, the plate with the projecting liquid level of the culture medium facing down was held with clean tweezers or the like and the projections of the culture medium were brought into contact with the surface of an α-MEM culture medium (Sigma) filling a separate larger vessel that was supplemented with heat-inactivated fetal bovine serum (55° C.×30 min) to a final concentration of 10%; the cell masses were allowed to precipitate under their own weight into the culture medium in the larger vessel, thereby recovering embryoid bodies or the cell masses derived from the embryonic stem cells.

The recovered embryoid bodies were cultured in a non-cell-adhesive dish (Asahi Techno Glass, sterile Petri dish #SH90-15; or Eiken Chemical Co., Ltd., sterile rectangular Petri dish type 2) for an additional 2 or 3 days. The cultured embryoid bodies were recovered into a centrifugal tube and after replacing the suspension with a serum-free culture medium (α-MEM culture medium (#MO644 of SIGMA) supplemented with an ITS solution (GIBCO #41400-045) after 1/100 dilution (the ITS solution used in the present invention contained 1 g/L of insulin, 0.55 g/L of transferrin, and 0.67 mg/L of selenium chloride)), the embryoid bodies were cultured in a cell adhesive, sterile culture dish (FALCON #353003).

Culture medium was changed every other day until the 15th day of culture for differentiation. To the sample at day 15, a mitochondrial indicator TMRM (Invitrogen #T668) was added at a final concentration of 10 mM, which was incubated for 2 hours. Thereafter, using a physiological buffer (116 mM NaCl, 20 mM Hepes, 12.5 mM $NaH_2PO_4$, 5.6 mM glucose, 5.4 mM KCl, 0.8 mM $MgSO_4$, pH 7.35) containing collagenase (Wortington Type 3) and trypsin (DIFCO #215240) each added at a final concentration of 0.1%, the cultured cells were dispersed to single cells with the culture medium being stirred. The sample, or the suspension of single cells, was loaded in a fluorescent activated cell sorter (FACS) to thereby recover highly fluorescent cell groups (WO 2006/022377). The purified cells were counted for the numbers of viable and dead cells by means of a hematocytometer. As it turned out, the proportion of the viable cells was about 75%.

Example 2: Preparation of Cell Masses Using Cardiomyocytes Derived from Mouse Embryonic Stem Cells The purpose of this Example was to know whether it was possible to prepare cell masses using the cardiomyocytes derived from mouse embryonic stem cell that were prepared in Example 1.

The purified, cardiomyocytes derived from mouse embryonic stem cell that were prepared in Example 1 were distributed in non-cell-adhesive, round bottom 96-well plates (SUMITOMO BAKELIKE CO., LTD.; CELLFECTIGHT SPHEROID) such that 10,000, 5,000, 2,500, 1,250, 625 or 313 cells would be present in each well. The culture medium was α-MEM supplemented with 10% fetal bovine serum. The distributed cells were observed over time; 10 hours later, eels masses formed and started to beat spontaneously in a synchronous manner. Twenty-four hours later, the cell masses each assumed a nearly perfect spherical shape and 10 days later, rhythmic, synchronous and spontaneous beating occurred (FIG. 1).

These results showed that, after the cardiomyocytes derived from mouse embryonic stem cells were dispersed to single cells, they could be reaggregated to form cell masses.

Example 3: Preparation of Cell Masses Using Cardiomyocytes Derived from Marmoset Embryonic Stem Cells The purpose of this Example was to know whether it was possible to prepare cell masses using cardiomyocytes derived from marmoset embryonic stem cell that were prepared in accordance with the method of Example 1.

The marmoset embryonic stem cells were obtained from the Central Institute for Experimental Animals (Sasaki E, et al., Stem Cells. 2005; 23(9): 1304-13). Using mouse embryonic fibroblasts (MEF) that had been growth-inactivated by mitomycin C treatment, these marmoset embryonic stem cells were cultured such that they would remain undifferentiated. The culture medium was composed of KO-DMEM (GIBCO), 20% KO-SERUM (GIBCO), 1.6 mM L-glutamine, 0.1 mM non-essential amino acids (MEM), 0.2 mM p-mercaptoethanol (2-ME; Sigma), 100 IU/ml penicillin, 100 µg/ml streptomycin sulfate, and 8 ng/ml each of a recombinant human leukemia inhibiting factor (LIF; Chemicon) and a recombinant human basic fibroblast growth factor (bFGF: Peprotech). For serial passage, colonies of embryonic stem cells were separated by treatment with 0.1% type III collagenase (Wortington) at 37° C. for 10 minutes.

Subsequently, in order to separate the embryonic stem cells from MET, the culture medium containing cell masses was passed through a mesh with a pore size of 100 µm, which was then passed through a mesh with a pore size of 40 µm to discard the undersize fraction; the cell masses in the oversize fraction were recovered. The recovered cell masses were those of pure embryonic stem cells. For differentiation, 50-1,000 embryonic stem cells per EB were cultured as embryoid bodies on a non-cell-adhesive bacterium dish (Asahi Techno Glass; sterile Petri dish) for a total of 25-30 days so that they differentiated into embryoid bodies including cardiomyocytes. The culture medium used for this differentiation was the same as identified above, except that it did not contain bFGF, i.e., it was composed of KO-DMEM (GIBCO), 20% KO-SERUM (GIBCO), 1.6 mM L-glutamine, 0.1 mM non-essential amino acids (MEM), 0.2 mM β-mercaptoethanol (2-ME; Sigma), 100

IU/ml penicillin, 100 μg/ml streptomycin sulfate, and 8 ng/ml of a recombinant human leukemia inhibiting factor (LIF; Chemicon).

One or two months after their preparation, the embryoid bodies were picked up and treated by the method described in WO 2006/022377 to purify the cardiomyocytes. To be more specific, the embryoid bodies were treated with collagenase and trypsin to give disaggregated single cells. To the culture medium as a cell suspension, a mitochondrial indicator TMRM (Invitrogen #T66) was added at a final concentration of 10 mM and the mixture was left to stand at 37° C. for 15 minutes, washed three times, and immediately subjected to FACS analysis. Cells (cardiomyocytes) displaying a higher fluorescent intensity than the principal cell population were separated and recovered.

The separated cardiomyocytes were treated by the same method as in Example 2 to prepare cell masses of cardiomyocytes. To be more specific, the purified cardiomyocytes derived from marmoset embryonic stem cells were distributed in a non-cell-adhesive, round bottom 96-well plate (SUMITOMO BAKELIKE CO., LTD.; CELLFECTIGHT SPHEROID) such that 2,000 cells would be present in each well. The distributed cells were observed over time; 24 hours later, cell masses formed (FIG. 2A) and started to beat spontaneously in a synchronous manner. Forty-eight hours later, the cell masses each assumed a nearly perfect spherical shape (FIG. 2B) and 10 days later, rhythmic, synchronous and spontaneous beating occurred (FIG. 2).

These results showed that, after the cardiomyocytes derived from marmoset embryonic stem cells were dispersed to single cells, they could be reaggregated to form cell masses.

Example 4: Measurement of Cell Survival Rate for Cell Masses Formed by Using Cardiomyocytes Derived from Muse Embryonic Stem Cells and Comparison with the Result of Adhesive Culture The purposes of this Example were to study the adhesive substrate with the strength of protective action under plane culture conditions being used as an index, and to compare the survival rate of purified, embryonic stem cell-derived cardiomyocytes between plane adhesive culture and cell mass culture; the plane adhesive culture was performed using serum having a strong cell protecting action, and the cell mass culture was performed in the condition with or without serum; the cell protecting action was found to be superior when cell mass culture was performed under serum-free conditions.

In Example 4, cardiomyocytes derived from mouse embryonic stem cells were purified in accordance with Example 1.

Figure 3A:
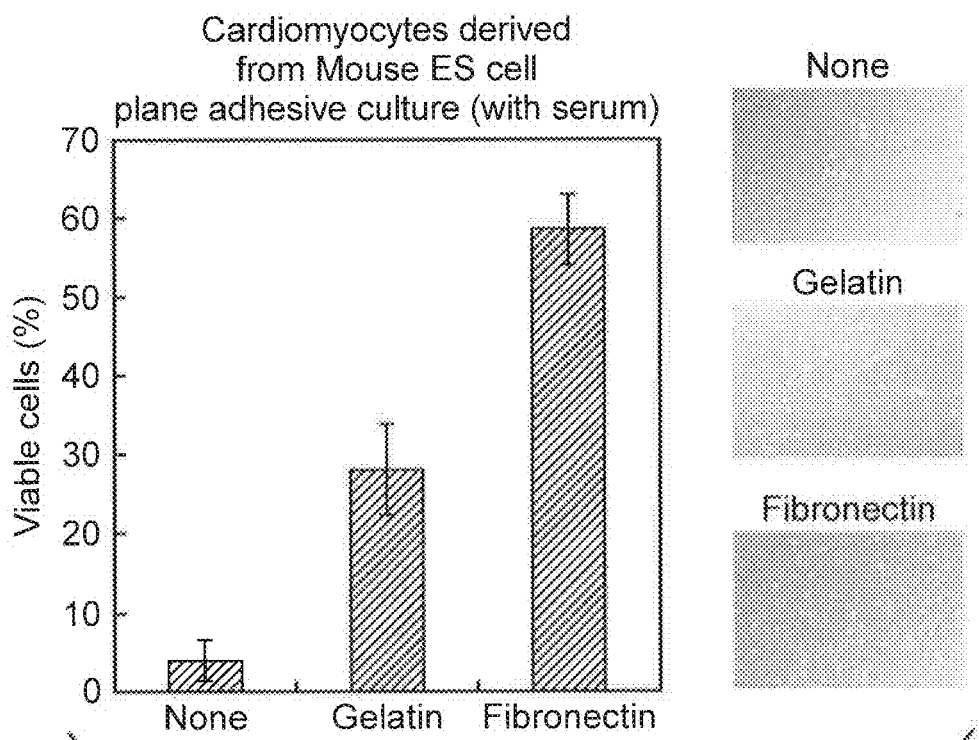
FIGS. 3A, 3B, and 3C show the results of plane culture of purified cardiomyocytes derived from mouse embryonic stem cells, in particular, the identification of an optimum adhesive substrate for use in plane culture based on comparison of the cell survival rate by adhesive substrates (FIG. 3A), and the comparison of cell masses and survival rate of cardiomyocytes of plane culture depending on the presence of serum in the culture medium (FIGS. 3B and 3C).
Figure 3B:
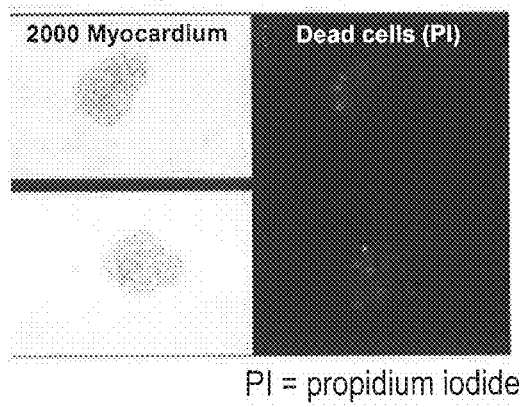
Figure 3C:
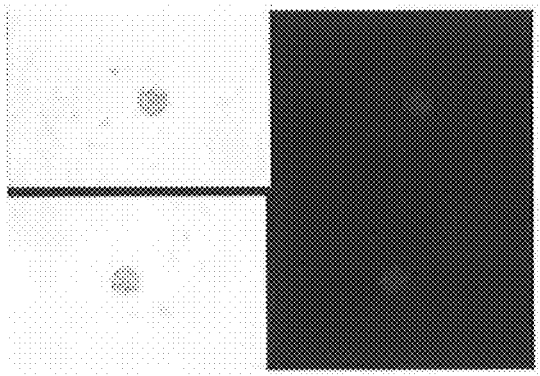

The purified cardiomyocytes were seeded in plastic culture dishes (product of BD), coated with either (1) gelatin or (2) fibronectin, in the presence of serum (FIG. 3A). In addition, with a view to forming cell masses, (3) the purified cardiomyocytes were distributed in a non-cell-adhesive, round bottom 96-well plate in accordance with Example 2 such that 1,000 cells would be present in one well and the suspensions were centrifuged at 120 g tor 5 minutes. Further in addition, (4) the purified cardiomyocytes were distributed in a non-cell-adhesive, round bottom 96-well plate in accordance with Example 2 except for using serum-free conditions to construct cell masses, such that 1,000 cells would be present in each well and the suspensions were centrifuged at 120 g for 5 minutes. The samples of (1) to (4) were cultured in the same incubator for 12 hours and 4 days. Four days later, the number of cells adhering to each dish (the viable cell count) and that of non-adherent but suspending cells (dead cell count) were measured. The results are depicted in FIG. 3 (see FIG. 3A for the conditions of (1) and (2), and also see FIGS. 3B and 3C for the conditions of (3) and (4), respectively.)

As it turned out, the cell viability in cell mass culture under serum-free conditions was obviously higher than the maximum value for plane adhesive culture in the presence of serum (ea, 60% in the case of (2)), i.e., 99.2% viable in the case of (3) and 90.4% viable in the case of (4).

Example 5: Preparation of Cell Masses Using Cardiomyocytes Derived from Purified Mouse Embryonic Steal Cells and Detection of Contaminated Embryonic Stem Cells The purpose of this Example was to detect non-cardiomyocytes that were contaminated in cell masses formed of purified cardiomyocytes derived from mouse embryonic stem cells.

Cell masses of purified cardiomyocytes were prepared by the methods of Examples 1 and 2, provided that prior to the final seeding of the 96-well plate, 2% of undifferentiated embryonic stem cells were added to the suspension of cardiomyocytes. The cell masses were cultured in a serum-free α-MEM solution that contained 1 mg/ml of insulin and 10 nM of TMRM; 14 days later, fluorescent images and phase-contrast images were acquired from all wells.

Figure 4:
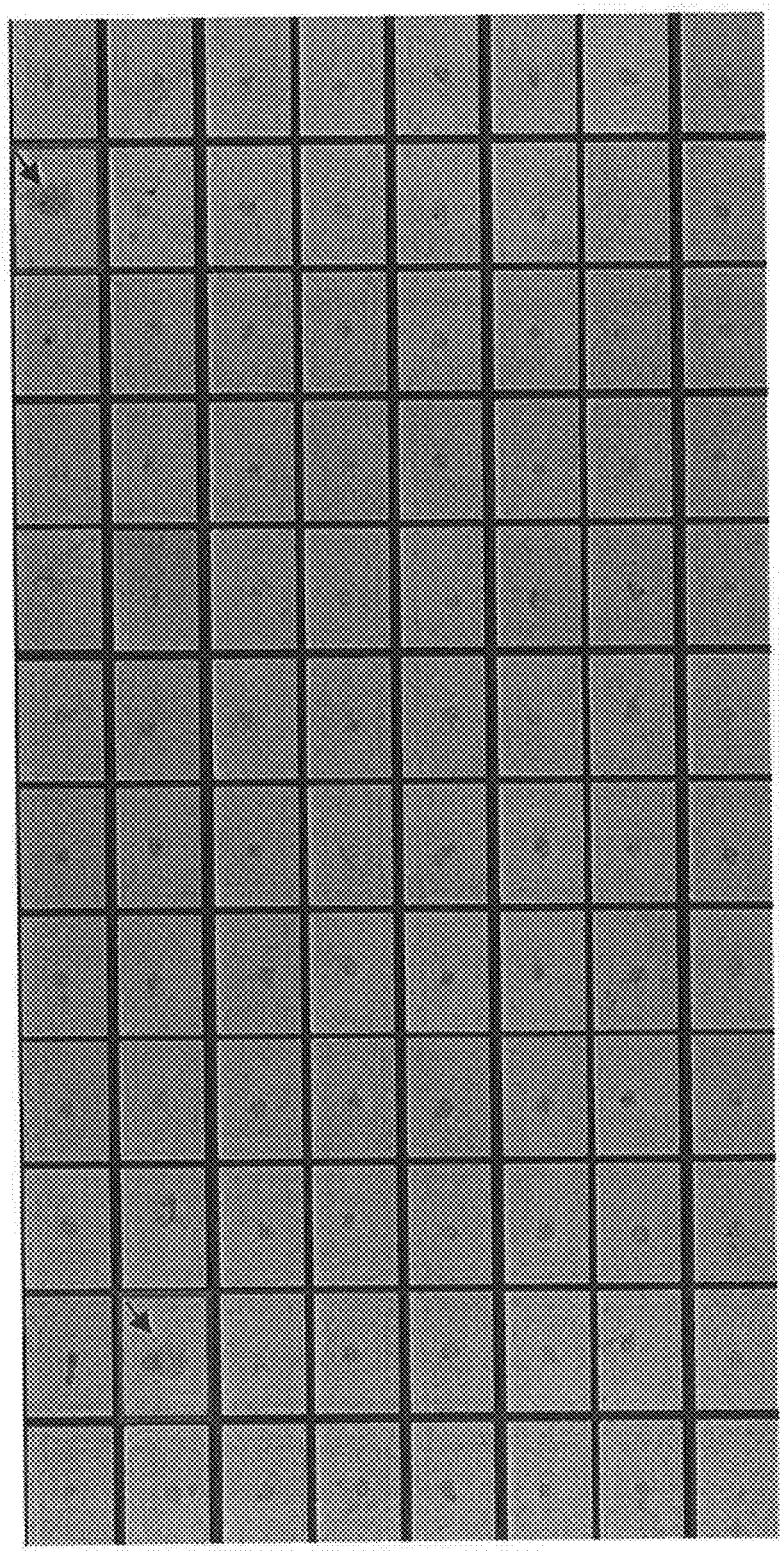
FIG. 4 shows method (1) of detecting embryonic stem cells that are contaminated in the cell masses formed of purified cardiomyocytes derived from mouse embryonic stem cells; the cell masses marked by the red frames were found to contain gigantic cell masses as a result of cell proliferation.
Figure 5A:
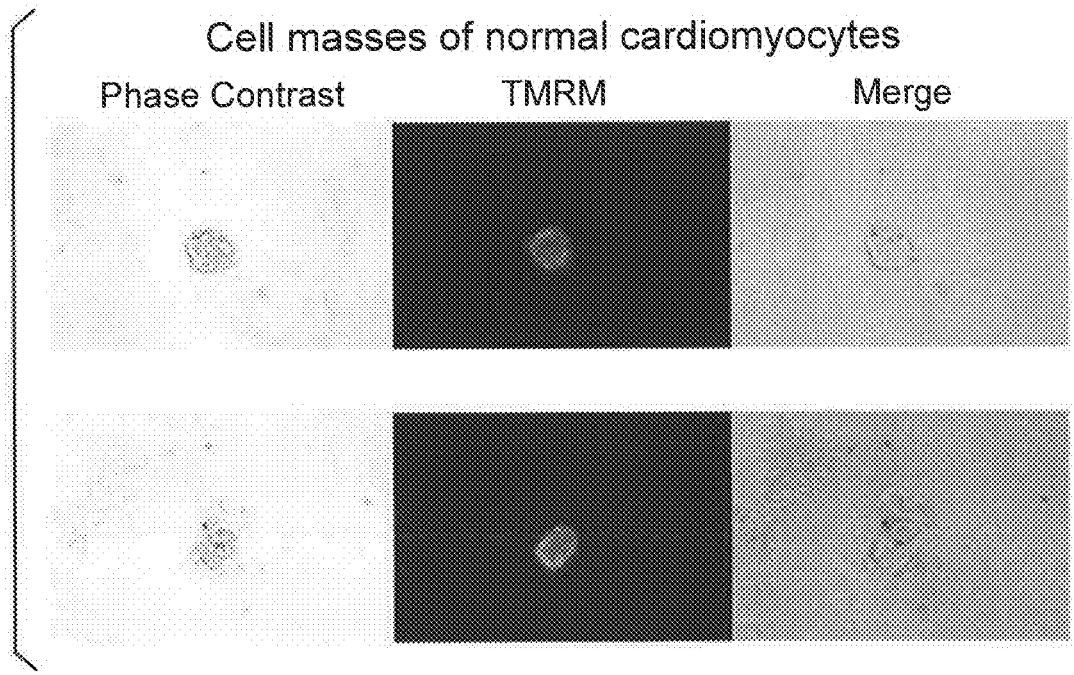
FIGS. 5A and 5B show method (2) of detecting embryonic stem cells that, are contaminated in the cell masses formed of purified cardiomyocytes derived from mouse embryonic stem cells; the contaminated and proliferated non-cardiomyocytes could be detected on the basis of a weak fluorescent signal derived from TMRM (a reagent that specifically stained mitochondria), making it clear that, in contrast with cell masses of normal cardiomyocytes (FIG. 5A), cell masses of abnormal cardiomyocytes (FIG. 5B) were contaminated by proliferated non-cardiomyocytes.
Figure 5B:
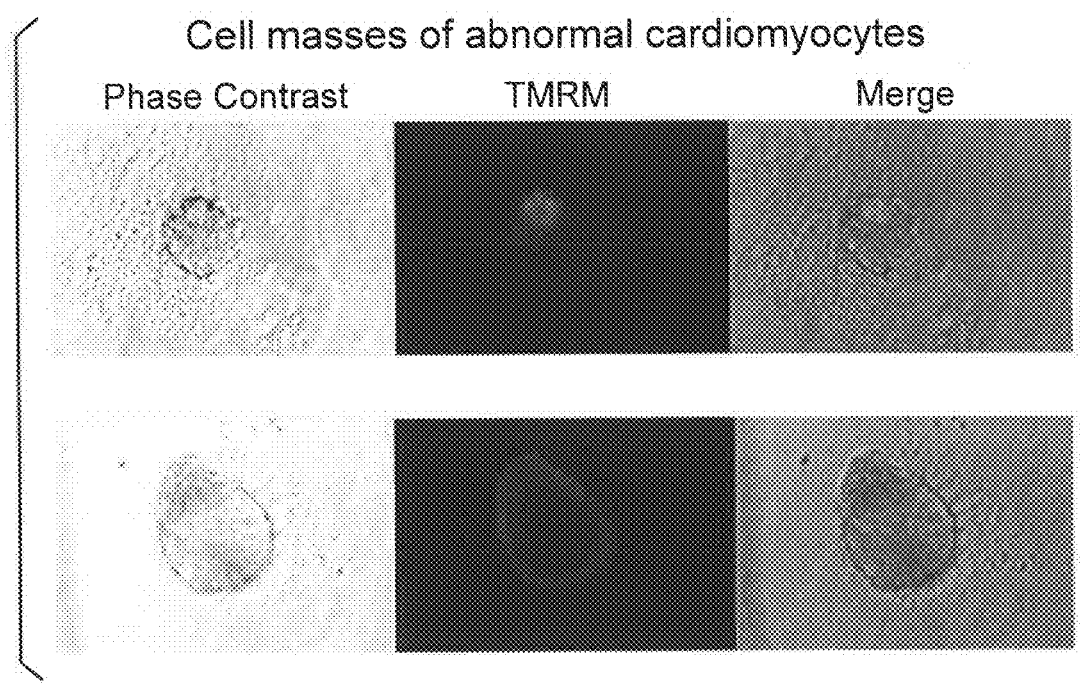

As a result, in two wells that accounted for about 2% of the wells, a larger cell mass (more than twice the size of normal cell masses) was observed (FIG. 4) and it was found that part of these non-spherical cell masses formed a cell population that emitted a weak, TMRM-derived fluorescent signal (i.e., non-cardiomyocytes) and which was composed of abnormal cardiomyocytes (FIG. 5B), The whole cell masses of normal cardiomyocytes emitted a TERM derived fluorescent signal (FIG. 5A).

Thus, the method provided by Example 5 enabled contaminant non-cardiomyocytes to be identified with high sensitivity.

Example 6: Preparation of Cell Masses Using Purified Cardiomyocytes Derived from Neonatal Rat Heart The purpose of this Example was to know whether it was possible to prepare cell masses using purified cardiomyocytes derived from neonatal rat heart.

Neonatal rats 0-2 days after birth were anesthetized with ether. The heart was excised and the cardiac tissue was dispersed into disaggregated cells with 0.1% collagenase (Wortington). The cells were stained with 10 nM TMRM and then treated by FACS to purify the cardiomyocytes.

The number of the purified cardiomyocytes was counted and cultured in a non-cell-adhesive 96-well dish (SUMITOMO BAKELITE) with 3,000 cells being seeded per well. The culture medium consisted of DMEM-high glucose (Invitrogen) supplemented with 10% FBS (JRH).

Figure 6A:
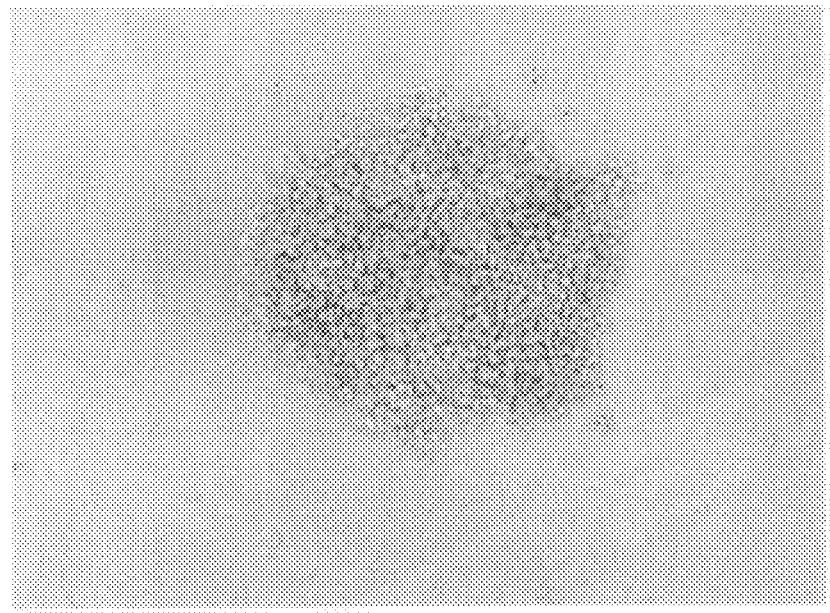
FIG. 6A shows that, when cultured on a non-cell-adhesive, round-bottom 96-well dish, purified cardiomyocytes derived from the neonatal rat heart were not capable of constructing cell masses even after 24 hours of culture.
Figure 6B:
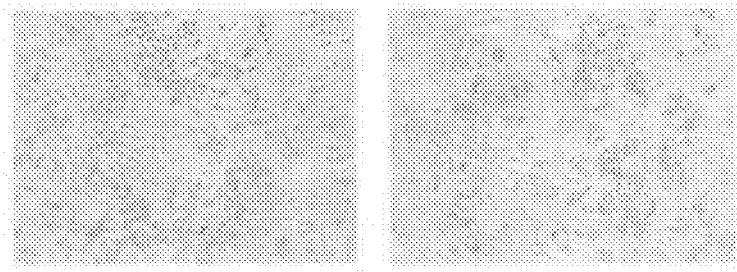
FIG. 6B shows that the purified cardiomyocytes derived from the neonatal rat heart, when cultured under serum-free conditions, did not form cell masses but died after the passage of 5 days.

The appearance of the cells after 24 hours of culture is depicted in FIG. 6. The purified cardiomyocytes derived from the neonatal rat heart did not form cell masses but aligned along the round bottom of each well (FIG. 6A). The purified cardiomyocytes derived from the neonatal rat heart at day 5 of culture were virtually dead (FIG. 6B) under the serum-free conditions (solely with the basal culture medium α-MEM (left panel of FIG. 6B, or with α-MEM+ITS (right panel of FIG. 6B)).

Example 7: Culture Medium Composition Optimum for Forming Celt Masses Using Cardiomyocytes Derived from Mouse Embryonic Stem Cells The purpose of this Example was to analyze the various properties of neonatal rat's primary cardiomyocytes and cardiomyocytes derived from mouse embryonic stem cells so as to find out a culture medium most suitable for the cardiomyocytes derived from embryonic stem cells.

Purified cardiomyocytes derived from mouse embryonic stem cells and purified neonatal rat cardiomyocytes were prepared as described above; they were then cultured in each of 10 different condition; one was solely composed of α-MEM and the other nine consisted of α-MEM+ITS, α-MEM+ITS+50 ng/ml bFGF (peprotech), α-MEM+ITS+50 ng/ml IGF-1 (Wako), α-MEM+ITS+50 ng/ml bFGF+50 ng/ml IGF-1, α-MEM+5% KSR (knockout serum replacement: Invitrogen), α-MEM+10% KSR (knockout serum replacement: Invitrogen), α-MEM+1% FBS (Equitech Bio), α-MEM+5% FBS, and α-MEM+10% FBS, respectively.

Figure 7A:
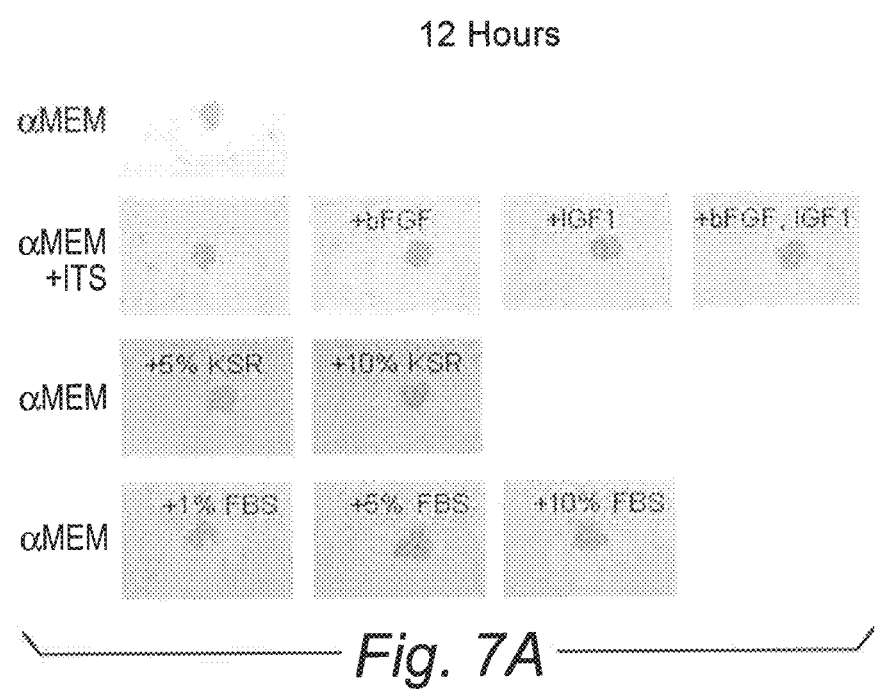
FIGS. 7A and 7B show the results of culture on a non-cell-adhesive, round-bottom 96-well dish using serum-free media to which ITS, bFGF and various other additives were added (FIG. 7A: 12 hours.

When the purified cardiomyocytes derived from mouse embryonic stem cells were cultured in a non-cell-adhesive, round bottom 96-well dish, cell masses formed in all culture media in just 32 hours (FIG. 7A). However, the neonatal rat cardiomyocytes failed to form cell masses even after 24 hours under all culture conditions. A culture medium supplemented with 10% serum is given as an example. After 4 days, the neonatal rat cardiomyocytes formed cell masses only in the media supplemented with 5% FBS and 10% FBS, respectively.

Figure 7B:
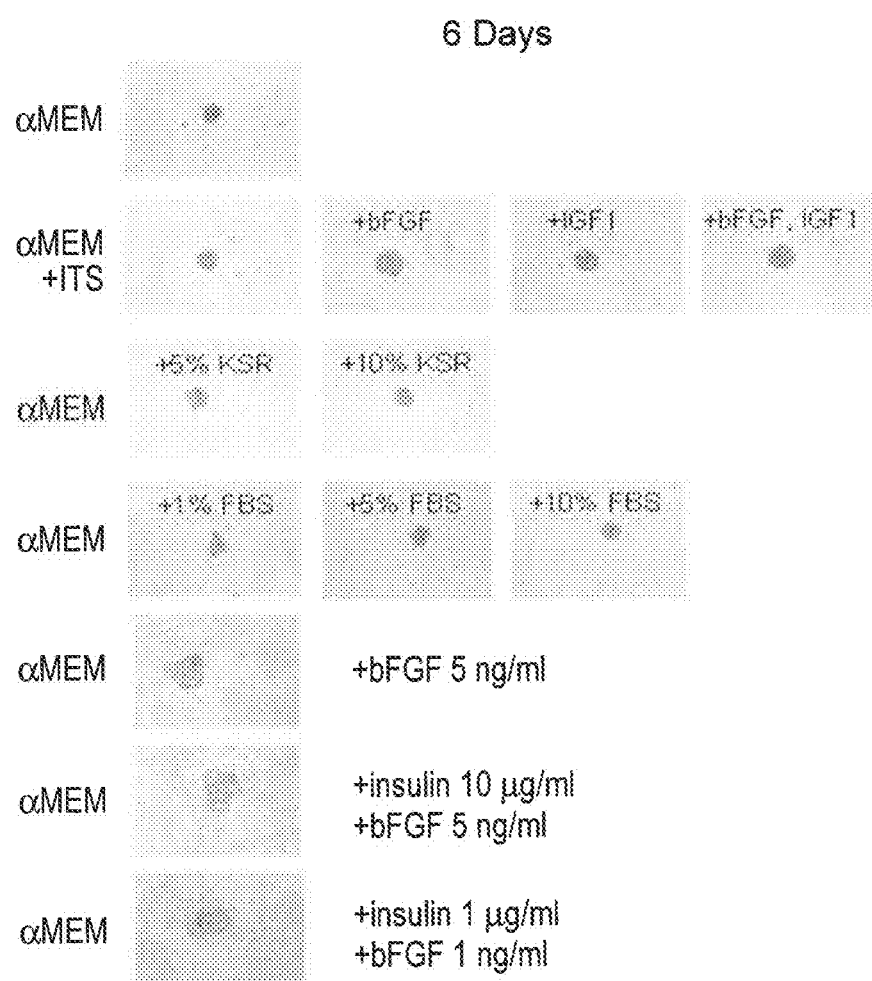
Figure 7C:
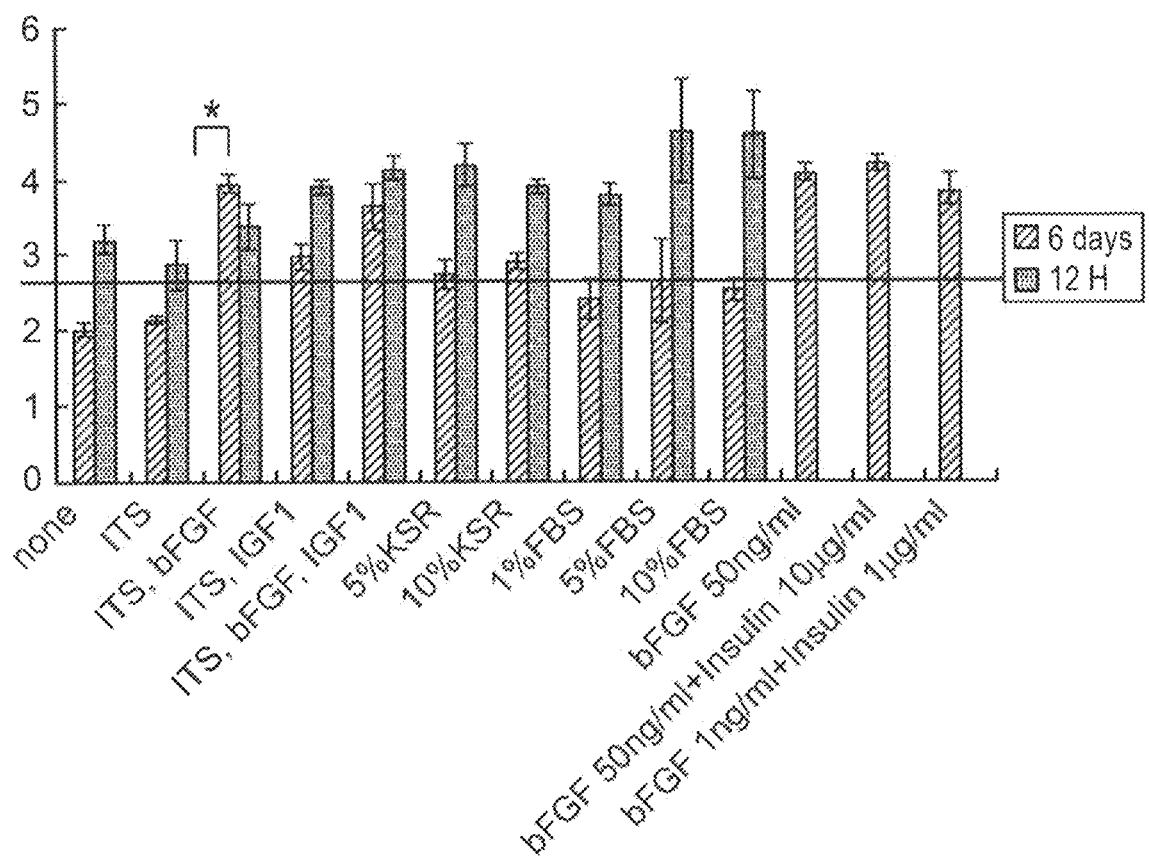
FIG. 7C shows that the cell protecting effect and growth promoting activity of those additives were detected by revealing effects which they had on the increase in the diameter of cell masses.

The cell masses of purified, cardiomyocytes derived from mouse embryonic stem cell that formed after 6 days of culture in a non-cell-adhesive, round bottom 96-well dish were observed (FIG. 7B); a significant increase in the diameter of cell masses, as compared to that of the cell masses just formed, was found only in the culture medium of α-MEM+TTS+50 ng/ml bFGF (see FIG. 7C, in particular, please refer to the column marked with the asterisk). Even in the serum-containing media, the diameter of cell masses was about one half the value for the early stage (FIG. 7C).

From the foregoing, it is believed that the serum-free culture medium supplemented with ITS and bFGF has a very strong cell protecting action and exhibits a unique property of inducing the proliferation of cardiomyocytes.

Example 8: Culture Medium Composition Optimum for the Formation of Cell Masses Using Cardiomyocytes Derived from Mouse Embryonic Stem Cells In Example 7, it was revealed that the serum-free culture medium supplemented with ITS and bFGF had a very strong cell protecting action and exhibited a unique property of inducing the proliferation of cardiomyocytes. Hence, Example 8 was performed in order to show what actions bFGF and insulin, a component of the ITS solution, would have on the increase in the diameter of cell masses.

Basically, experiments were conducted as in Example 7, except that the following culture media were used: α-MEM alone; α-MEM+50 ng/ml bFGF; α-MEM+10 μg/ml insulin 4-5 ng/ml bFGF: and α-MEM+1 μg/ml insulin+1 ng/ml bFGF.

Six days later, the cell masses of cardiomyocytes derived from mouse embryonic stem cells were observed: as the result, in each of α-MEM+50 ng/ml bFGF, α-MEM+10 μg/ml insulin+5 ng/ml bFGF, and α-MEM+1 μg/ml insulin+1 ng/ml bFGF, a significant increase in the diameter of cell masses was seen as compared to the cell mass in the culture medium consisting of α-MEM alone (FIG. 7B). In addition, the effect on contractile activity of the cardiomyocytes was strong and the same as what was achieved when ITS was added in Example 7.

From the foregoing, it is believed that the serum-free culture medium supplemented with bFGF or Insulin+bFGF has a very strong cell protecting action and exhibits a unique property of inducing the proliferation of cardiomyocytes.

Figure 8A:
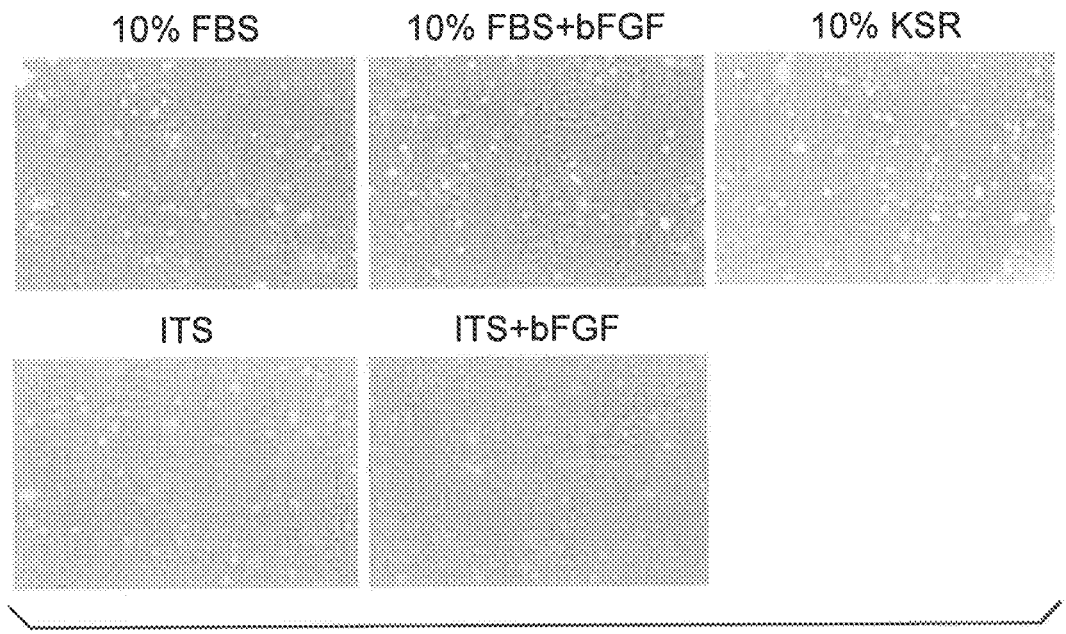
FIG. 8A shows the results of plane adhesive culture of purified cardiomyocytes derived from mouse embryonic stem cells on a cell culture dish coated with fibronectin after 5 days of culture.
Figure 8B:
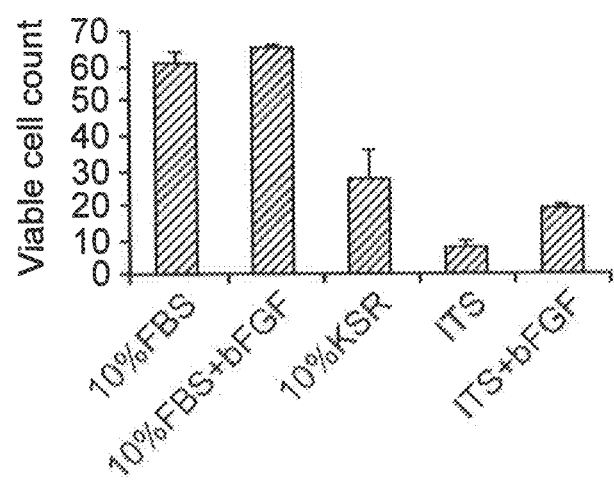
FIG. 8B shows that the cell viability was significantly low in the serum-free+ITS group and die ITS+bFGF group.

Example 9: Actions of "Serum-Free" and bFGF in Plane Adhesive Culture System of Purified Cardiomyocytes Derived from Mouse Embryonic Stem Cells Cardiomyocytes derived from mouse embryonic stem cells were purified in accordance with Example 1. The purified cardiomyocytes were seeded in the same numbers on fibronectin-coated cell culture dishes and subjected to plane adhesive culture in a variety of culture media. The various culture media all comprised α-MEM as a basal culture medium but they respectively had the following components added thereto: 10% FBS alone, 10% FBS+50 ng/ml bFGF, 10% KSR (knockout serum replacement: Invitrogen), ITS, and ITS+50 ng/ml bFGF. The cells seeded under those conditions were cultured for a total of 5 days and then photographed (FIG. 8A). As it turned out, the serum-free ITS and ITS+bFGF groups had significantly lower cell viability than the groups added with 10% FBS or 10% KSR.

Example 10: Transplantation of Purified Cardiomyocytes Derived from Mouse Embryonic Stem Cell into Myocardial Tissue of Immunodeficient Rat and Measurement of their Engraftment Rate To begin with, the following experiment was conducted in order to measure the survival rate of purified, cardiomyocytes derived from mouse embryonic stem cell tor the case where the reaggregation method was not applied.

A total of $2 \times 10^5$ cells were transplanted into the left ventricular free wall of an immunodeficient mouse (NOD-SCID). Anesthesia was induced on the mouse with ether and maintained using air containing 2% isoflurane supplied through an artificial respirator. The mouse was subjected to thoracotomy (in the third intercostal space) under deep anesthesia and the cardiac sac was ruptured with tweezers to expose the heart. Physiological saline (30 μl) containing cell masses of cardiomyocytes was injected through a syringe with a 30 G needle. For injection, the needle was inserted into the cardiac apex, from which it was advanced through the cardiac free wall by approximately 3 mm toward the cardiac base. After the transplantation, the chest was closed quickly and, after the recovery of spontaneous beating, the mouse was returned into the cage.

Three weeks after the transplantation, the heart was fixed under perfusion and frozen sections were prepared. The sections were immunostained with an anti-sarcomeric actinin antibody and fluorescent microscopic images were taken (FIG. 9A). As it turned out, viable cell transplants were barely seen and only the reaction with the tracer red dye could be found (FIGS. 9A and 9D).

In the next place, cell masses each consisting of 2000 cardiomyocytes as constructed under the serum-free conditions described in Example 7 (a total number of $2 \times 10^5$ cells) were transplanted into the left ventricular free wall of an immunodeficient mouse (NOD-SCID). The transplantation was carried out as in the experiment described above and 3 weeks later, the heart was fixed under perfusion and frozen sections were prepared. The sections were immunostained with an anti-sarcomeric actinin antibody and fluorescent microscopic images were taken (FIG. 10). Based on the fluorescent microscopic images, the number of cells engrafted on the host cardiac tissue contained in one cell mass was counted.

Figure 11A:
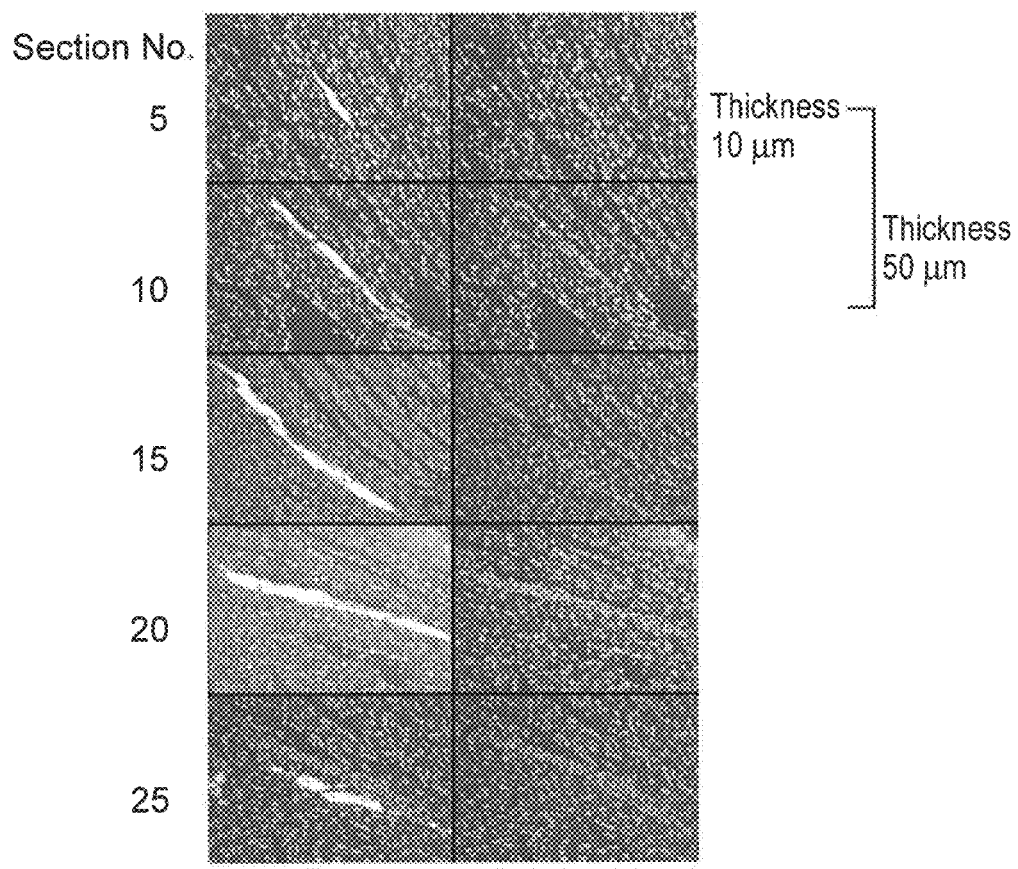
FIGS. 11A, 11B, 11C, and 11D show the results of transplantation to the heart of cell masses of purified cardiomyocytes derived from EGFP expressing mouse embryonic stem cells after reaggregation.
Figure 11B:
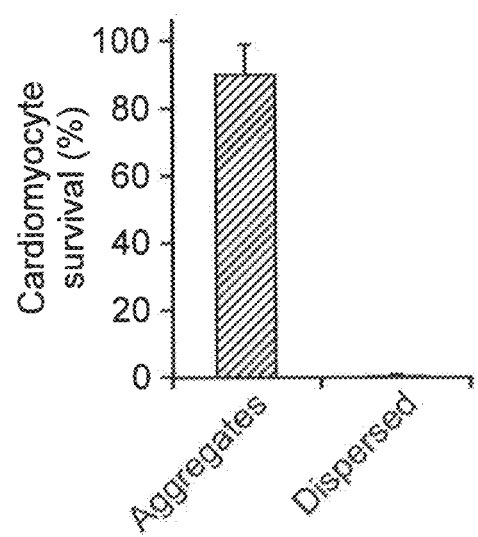

As it turned out, assuming that each of the transplanted cell masses accurately consisted of 2000 cardiomyocytes, 92.05±11.1% cardiomyocytes were found engrafted (n=4) (FIGS. 11A and 11B). In contrast, when the purified disaggregated cells were injected as such (as dispersed), no engrafted cells could be found. This result means that the post-transplantation engraftment rate of cardiomyocytes dramatically improved from 0% to 92%.

Figure 11C:
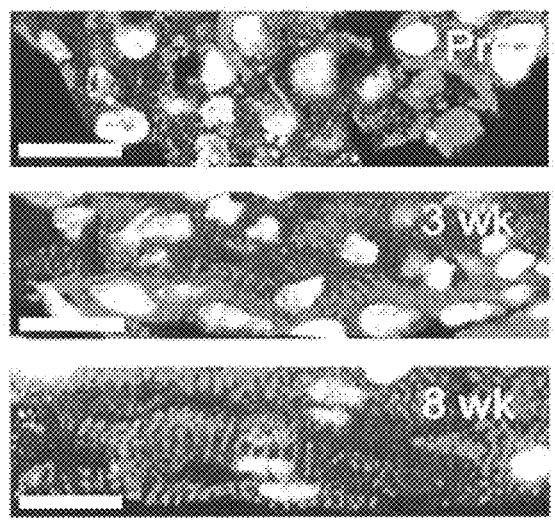
Figure 11D:
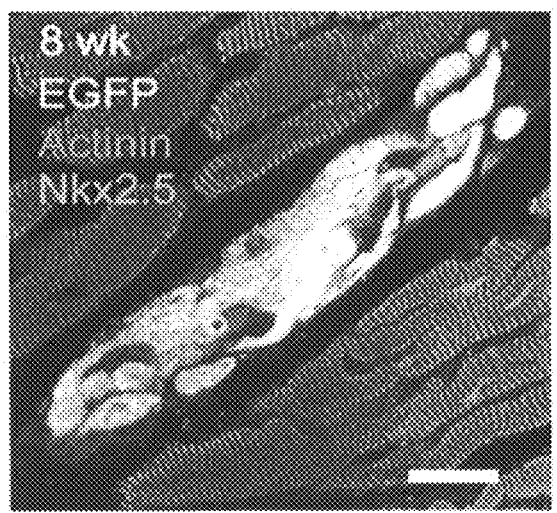

Further, with a view to verifying the change in cardiomyocytes during long-term transplantation, investigation based on immunostaining of the heart was performed 3 and 8 weeks after the transplantation. As it turned out, the cytoplasm volume of cardiomyocytes increased markedly 3 and 8 weeks after the transplantation, as compared with the cardiomyocytes before the transplantation ("Pre" in FIG. 11C), and what is more, the transplanted cardiomyocytes aligned in the same direction as the cardiomyocytes in the host (FIGS. 11C and 11D). This shows that the transplanted cell masses of cardiomyocytes matured in the host cardiac tissue.

Example 11: Preparation of Cell Masses Using Purified Cardiomyocytes Derived from Marmoset Embryonic Stem Cells The purpose of this Example was to prepare cell masses of purified cardiomyocytes derived from marmoset embryonic stem cell under serum-free conditions either with the addition of ITS or KSR.

Figure 12A:
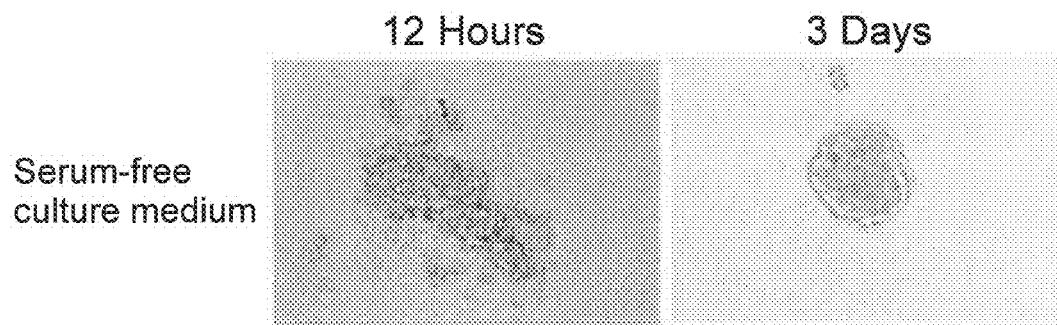
FIGS. 12A, 12B, and 12C show the result of preparing cell masses of purified cardiomyocytes derived from marmoset embryonic stem cells under a serum-free condition (FIG. 12A), a condition of serum-free and supplemented with KSR (FIG. 12B), and a condition of serum-free and supplemented with ITS (FIG. 12C).
Figure 12B:
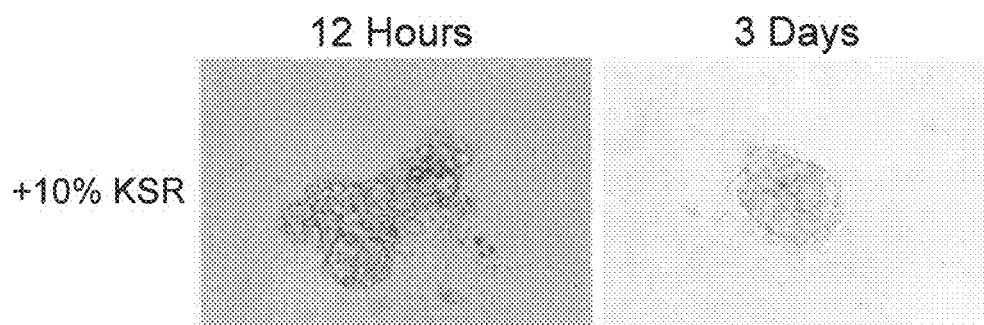
Figure 12C:
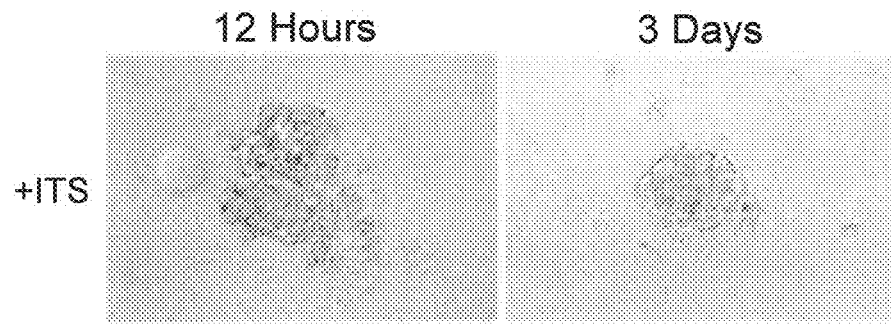

Briefly, cell masses of purified cardiomyocytes derived from marmoset embryonic stem cells were prepared in accordance with Example 3, provided that cell masses were cultured in a serum-free culture medium alone (FIG. 12A) or a serum-free culture medium supplemented with 10% KSR (FIG. 12B) or ITS (FIG. 12C). The cell masses constructed either 12 hours or 3 days after the start of transplantation are shown in FIG. 12.

Figure 13:
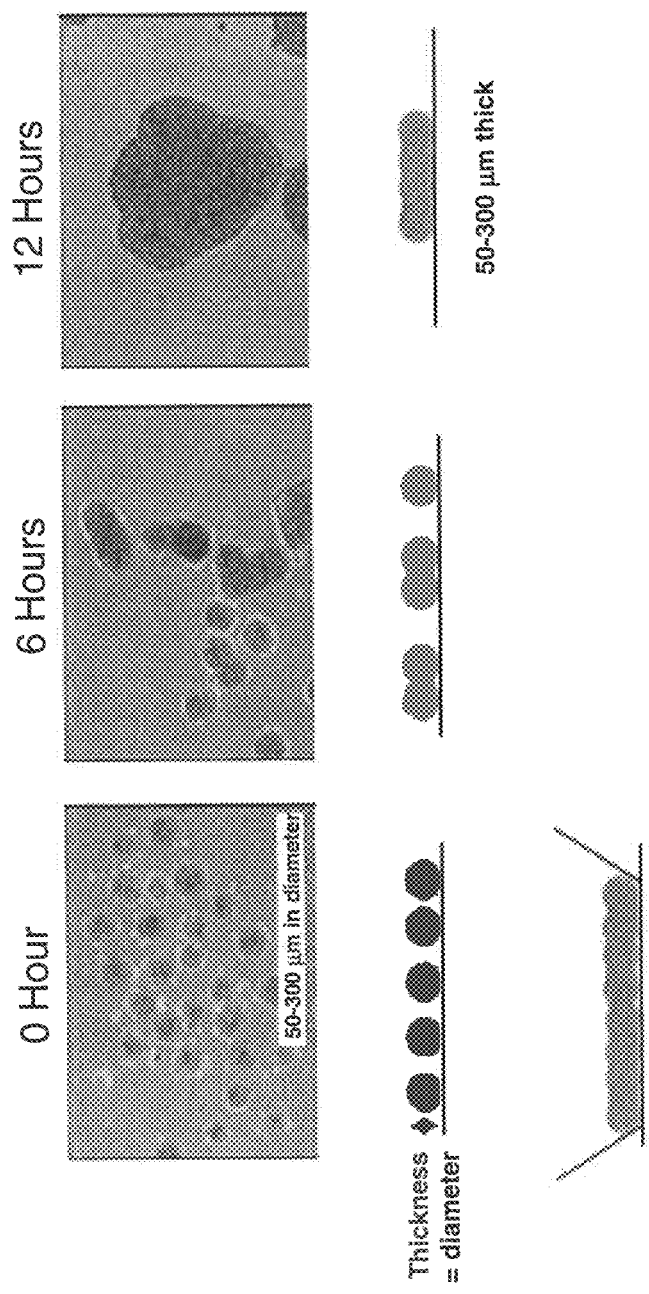
FIG. 13 shows the preparation of cardiomyocyte sheets of desired sizes having desired thicknesses using cell masses of purified cardiomyocytes derived from marmoset embryonic stem cells.

Example 12: Construction of "Thick" Cell Sheet Using Cell Masses of Purified Cardiomyocytes Derived from Marmoset Embryonic Stem Cells The cell masses of purified cardiomyocytes derived from marmoset embryonic stem cell that were prepared in Example 11 were suspension cultured in the same plane. With the lapse of time over the period of from 0 to 12 hours, adjacent cell masses are conjugated together to form a "thick" cell sheet of cardiomyocytes. Example 12 describes a model experiment intended to demonstrate the applicability of the method of the present invention. In actual application embodiments, cell masses in a desired size of purified cardiomyocytes derived from embryonic stem cells can be used in a desired number to construct a cell sheet of a desired size (FIG. 13). In addition, a cell sheet of a desired thickness can be formed depending on the size of the cell masses to be used.

Example 13: Transplantation of Cardiomyocytes Derived from Human Embryonic Stem Cell to the Immunodeficient Mouse Heart In this Example, experiments were to determine whether the cell masses of cardiomyocytes which were prepared by differentiating human embryonic stem cells into cardiomyocytes would have the ability to be engrafted in the cardiac tissue.

The human embryonic stem cells were obtained from the Stem Cell Research Center, adjunct facilities to the Institute for Frontier Medical Sciences, Kyoto University (the Embryonic Stem Cell Center sponsored by the National Bio-resource Project).

Using mouse embryonic fibroblasts (MEF) that had been growth-inactivated by mitomycin C treatment, these human embryonic stem cells were cultured such that they would remain undifferentiated. The culture medium was composed of F12/DMEM (1:1) (SIGMA, Lot No. D6421), 20% KO-SERUM (GIBCO), 3.6 mM L-glutamine, 0.1 mM non-essential amino acids (MEM), 0.1 mM β-mercaptoethanol (2-ME; Sigma), 100 IU/ml penicillin, 100 µg/ml streptomycin sulfate, and a recombinant human basic fibroblast growth factor (bFGF; Peprotech). For serial passage, colonies of embryonic stem cells were separated by treatment with 0.1% type III collagenase (Wortington) at 37° C. for 10 minutes.

Subsequently, in order to separate the embryonic stem cells from MEF, the culture medium containing cell masses was passed through a mesh with a pore size of 40 um and the cell masses in the oversize fraction were recovered. The recovered cell masses were those of pure embryonic stem, cells. For differentiation, 50-1,000 embryonic stem cells per EB were cultured as embryoid bodies on a non-cell-adhesive bacterium dish (Asahi Techno Glass; sterile Petri dish) for a total of 15-30 days so that they differentiated into embryoid bodies including cardiomyocytes. The culture medium used for this differentiation was the same as identified above, except that it did not contain bFGF, i.e., it was composed of F12/DMEM (1:1) (SIGMA, Lot No. D6421), 20% KO-SERUM (GIBCO), 1.6 mM L-glutamine, 0.1 mM non-essential amino acids (MEM), 0.1 mM β-mercaptoethanol (2-ME; Sigma), 100 IU/ml penicillin, and 100 µg/ml streptomycin sulfate.

Figure 14:
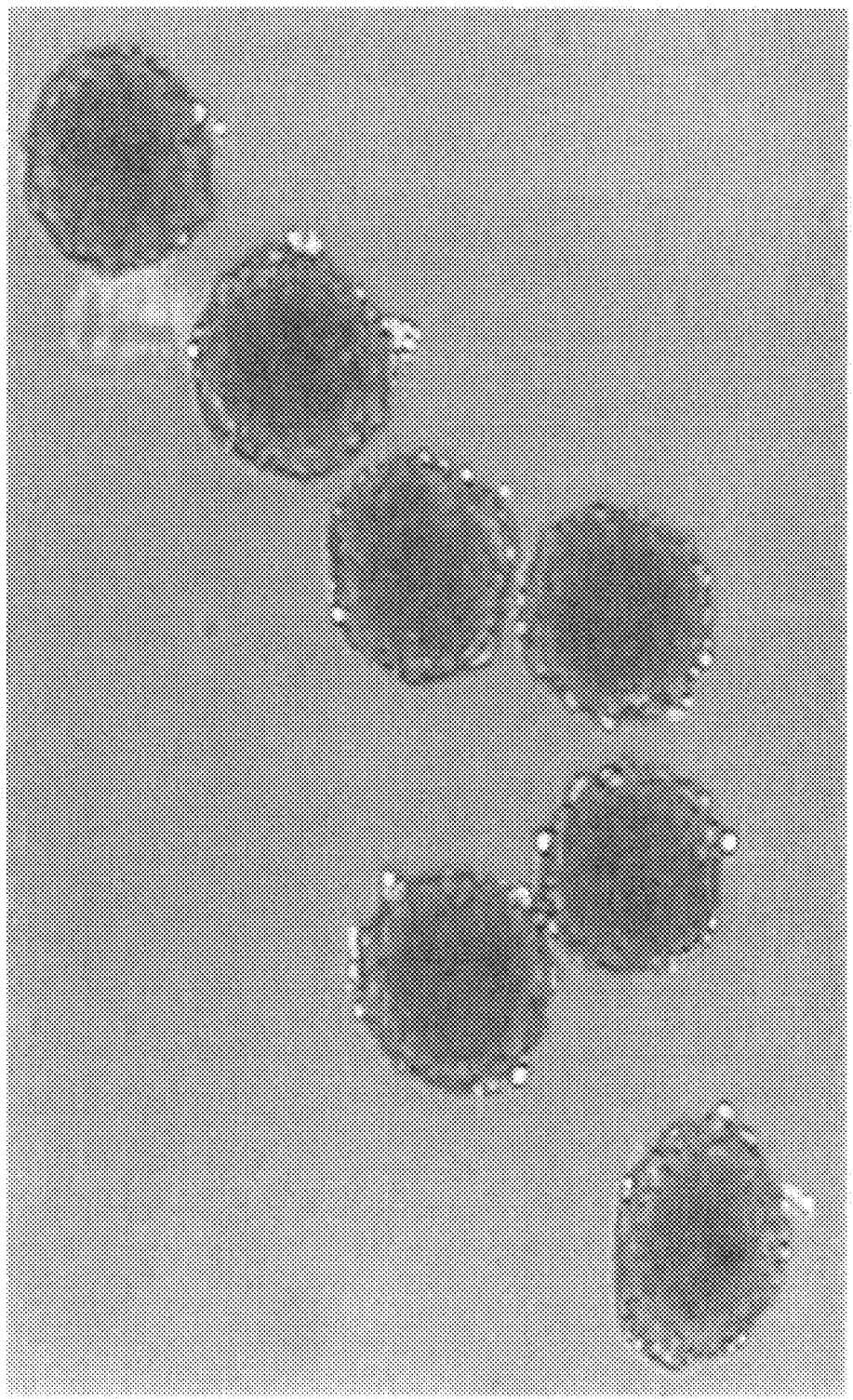
FIG. 14 shows that cell masses of cardiomyocytes derived from purified human embryonic stem cells could be prepared under a serum-free condition.

Cardiomyocytes derived from human embryonic stem cells were purified in accordance with Example 1. Then, in accordance with the results of Example 8, cell masses each containing 1000 purified cardiomyocytes were prepared using a serum-free α-MEM solution that contained 1 µg/ml insulin and 1 ng/ml bFGF (see FIG. 14).

Further, the cell masses were transplanted into the cardiac tissue of an immunodeficient mouse in accordance with Example 10. Two weeks after the transplantation, frozen sections were prepared in accordance with Example 10. The thus prepared sections were immunostained with Nkx2.5 and an anti-sarcomeric actinin antibody and fluorescent microscopic images were obtained.

Figure 15:
FIG. 15 shows that cardiomyocytes derived from human stem cells that were transplanted to the heart of immunodeficient mice could survive in the cardiac tissue for 2 weeks.

Some cell masses were found to be stained with the red dye used as a tracer of the transplanted cells. The sections were detected for the Nkx2.5 and anti-sarcomeric actinin antibody by an immunological method. The result is shown in FIG. 15. The transplanted cells, being stained with the red tracer dye, were shown to be predominantly red-colored, immunostaining with actinin also showed the staining of the striation. It was also shown that Nkx2.5, a marker of cardiomyocytes, was predominantly found in the nuclei of the transplanted cardiomyocytes. This is a phenomenon peculiar to immature cardiomyocytes. In addition, the nuclei of cardiomyocytes derived from human embryonic stem cells are larger than surrounding mouse cardiomyocytes and, hence, can be distinguished from the latter (FIG. 15).

Figure 16:
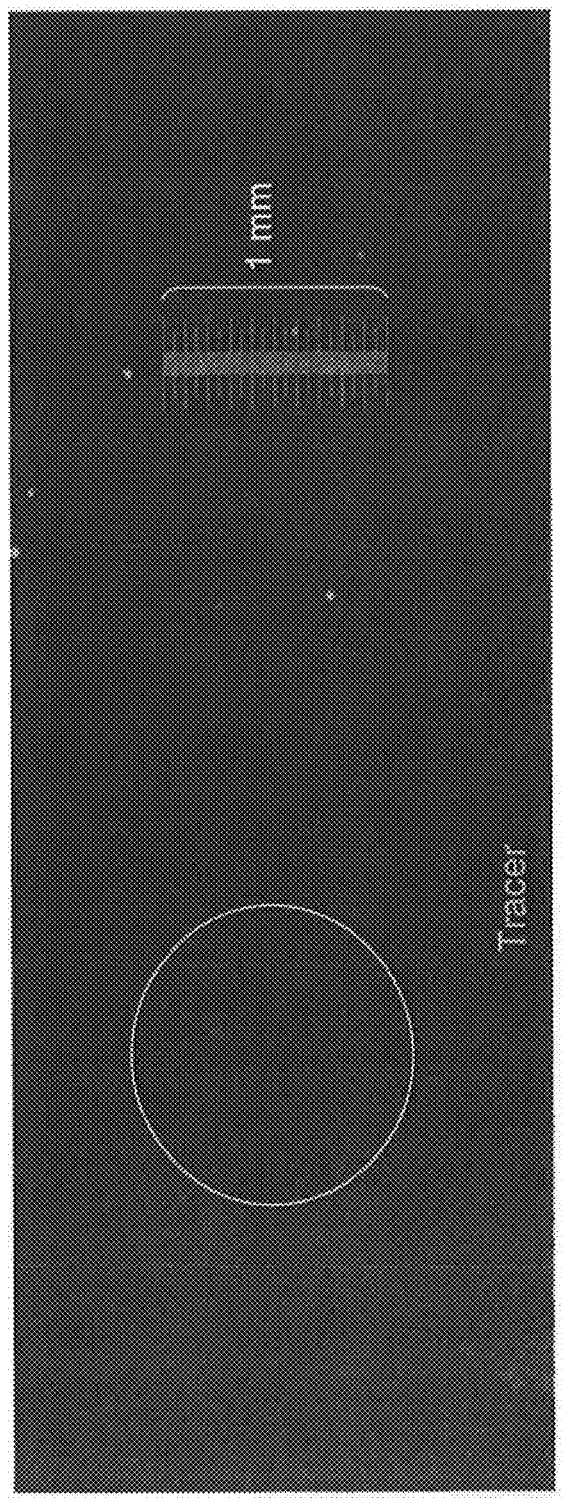
FIG. 16 shows that cardiomyocytes derived from human stem cells that were transplanted to the heart of immunodeficient mice could survive in the cardiac tissue for 5 weeks, as demonstrated by a red dye used to trace the transplanted cells.
Figure 17:
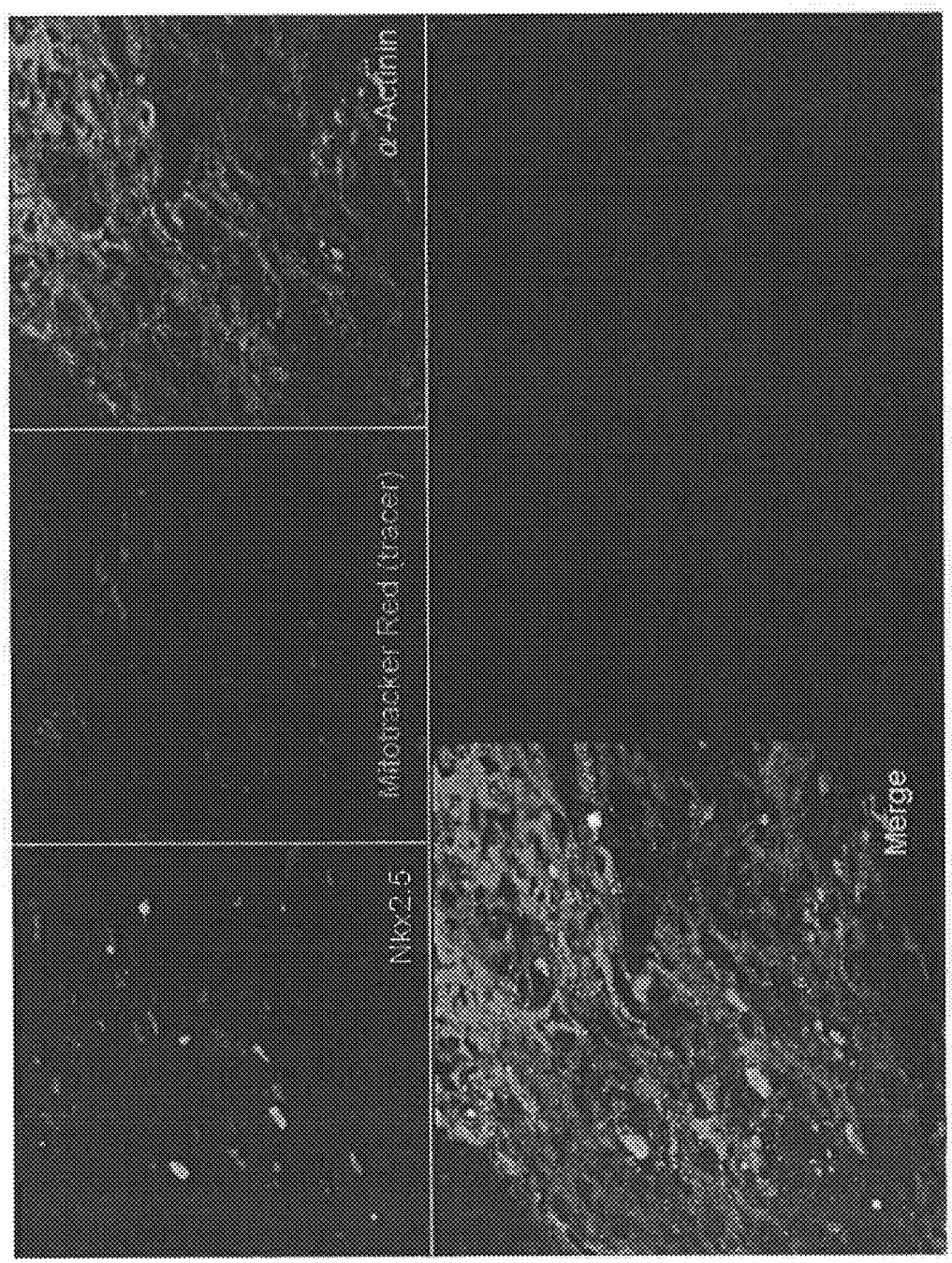
FIG. 17 shows that cardiomyocytes derived from human stem cells that were transplanted to the heart of immunodeficient mice could survive in the cardiac tissue for 5 weeks, as demonstrated by a dye (Microtracker Red: red color), Mkx 2.5 (watery blue), and an anti-sarcomeric actinin antibody (green) that were used to trace the transplanted cells.
Figure 18:
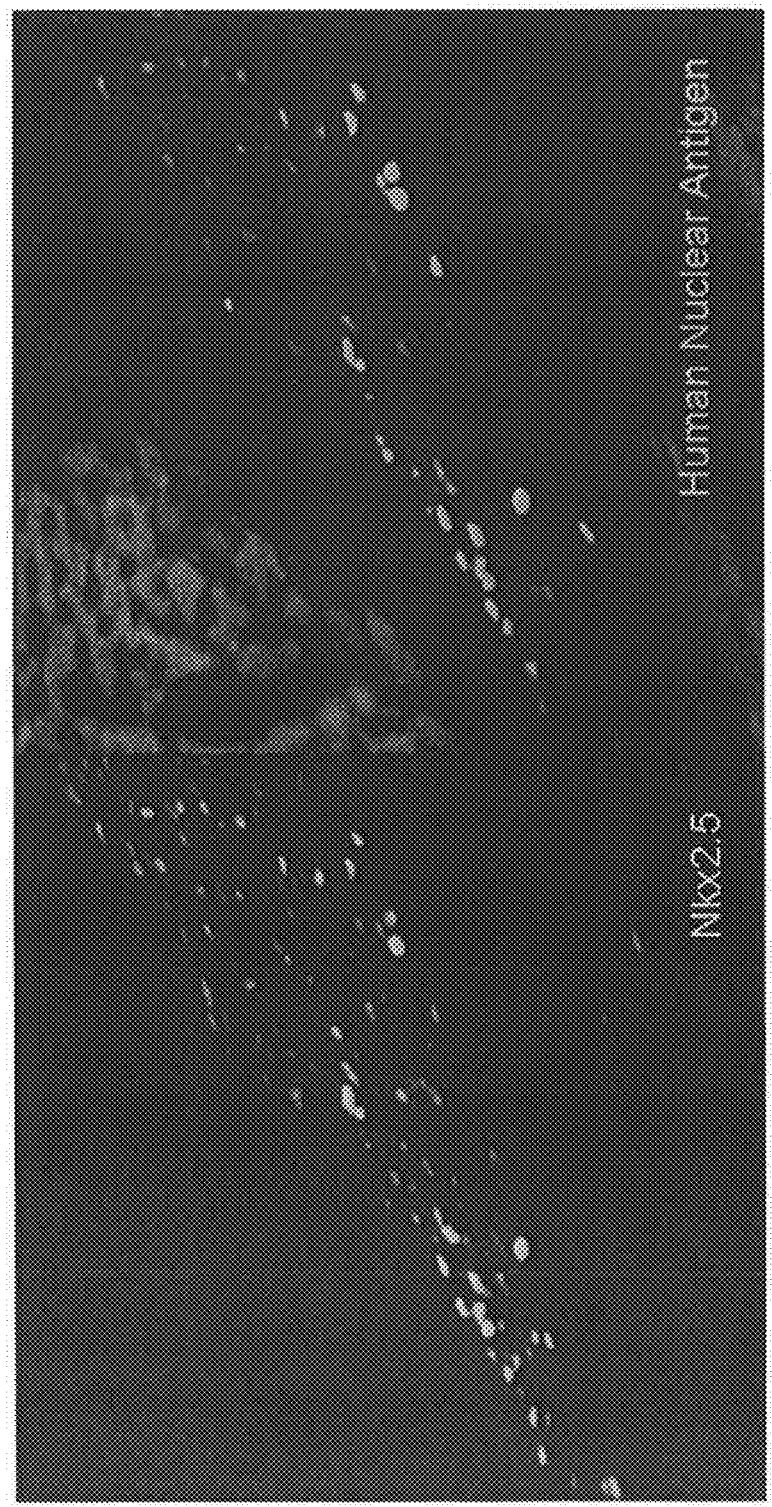
FIG. 18 shows that cardiomyocytes derived from human stem cells that were transplanted to the heart of immunodeficient mice could survive in the cardiac tissue for 5 weeks, as demonstrated by Mkx 2.5 (watery blue) and an anti-human antibody (green).

Further, 5 weeks after the transplantation, frozen sections were prepared in accordance with Example 10. Some cell masses were found to be stained with the red dye used as a tracer of the transplanted cells (FIG. 16). The thus prepared sections were immunostained with Nkx2.5 (watery blue) and an anti-sarcomeric actinin antibody (green) or with Nkx2.5 (watery blue) and an anti-human nuclear antigen (green: binding to an antigen that was not present in mouse nuclei but present only in primates) and fluorescent microscopic images were obtained. The results are shown in FIGS. 17 and 18. The mitochondria in the transplanted cells were stained with the tracer dye, allowing the red dye to be detected as spots. Immunostaining with actinin also showed the staining of the striation (FIG. 17). To show that these cell populations composing the same region were derived from human cells, detection was performed using an anti-human antibody and again it was demonstrated that the transplanted cells were human cells, in particular, cardiomyocytes that were co-stained with Nkx2.5 (FIG. 18).

Example 14: Preparation of Cell Masses Using Purified Cardiomyocytes Derived from Mouse Induced Pluripotent Stem (iPS) Cells The purpose of this Example was to prepare cell masses of purified cardiomyocytes derived from mouse iPS cells under serum-free conditions with or without addition of ITS or KSR.

The mouse iPS cells were assigned from the Institute for Frontier Medical Sciences, Kyoto University. Differentiation of the mouse iPS cells into cardiomyocytes was carried out as in Example 1. In that instance, it was found to be optimum that 1000 cells were used as the initial cells for composing one embryoid body.

Figure 19A:
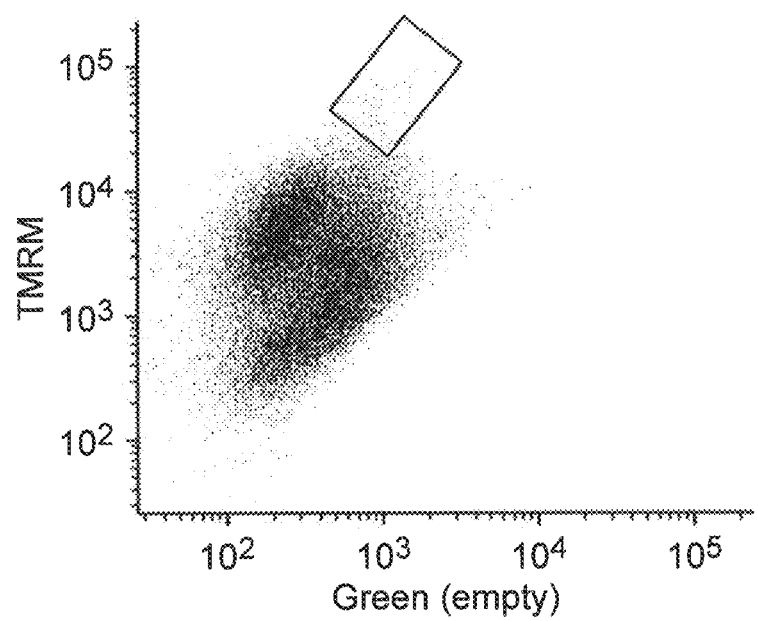
FIGS. 19A, 19B, and 19C show the results of preparing cell masses of purified cardiomyocytes derived from mouse iPS cells by culture under a serum-free condition, a condition of serum-free and supplemented with ITS, and a condition of serum-free and supplemented with KSR.
Figure 19B:
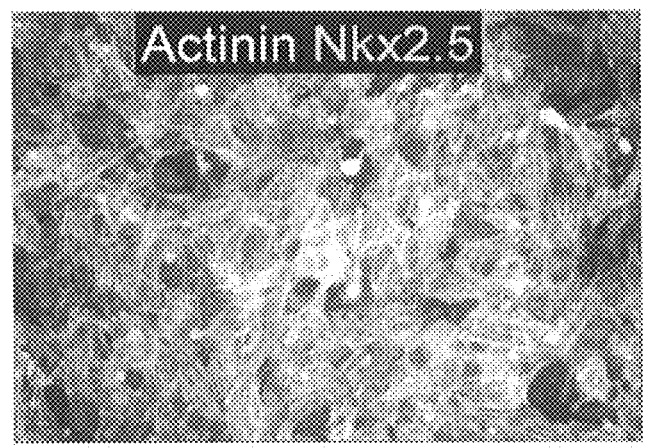
Figure 19C:
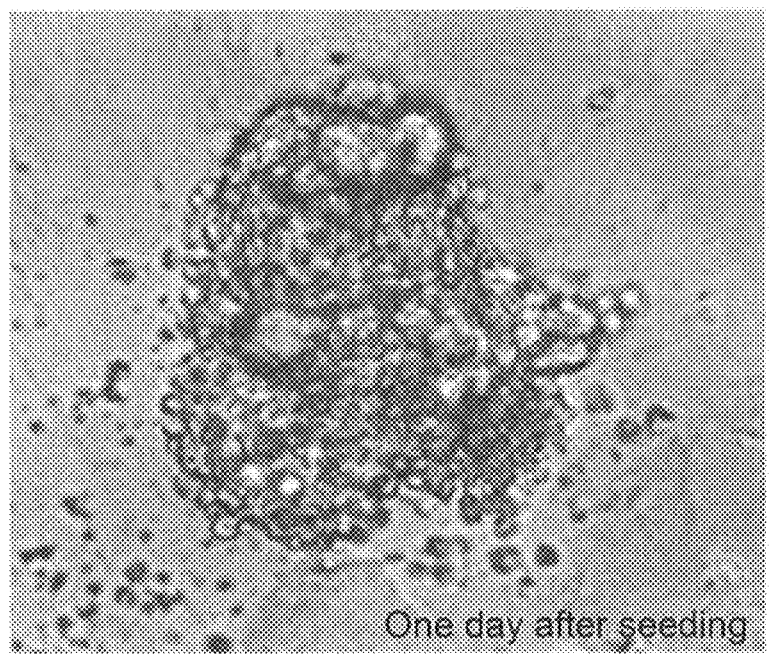

FIG. 19A shows the result of an FACS analysis conducted with the mitochondrial indicator TMRM in order to purify cardiomyocytes. The rectangle in the graph represents the region of cardiomyocytes. The thus purified cardiomyocytes were subjected to adhesive culture and immunostained (with actinin and Nkx2.5); the result is shown in FIG. 19B. Since the mouse iPS-induced cardiomyocytes were shown to form aggregated cell masses, it was revealed that the cell fractions recovered by FACS consisted of nearly 100% of cardiomyocytes. Further, FIG. 19C shows the appearance of the purified cardiomyocytes 24 hours after they were seeded in a non-cell-adhesive 96-well culture dish. In this case, a serum-free culture medium was used. As it turned out, the purified cardiomyocytes derived from mouse iPS cells could also be used to construct cell masses by the method of the present invention.

Example 15: Culture Medium Composition Optimum for Forming Cell Masses Using Cardiomyocytes Derived from Human Embryonic Stem Cells In Example 7, it was revealed that the serum-free culture medium supplemented with ITS and bFGF had a very strong protecting action on mouse-derived cells and exhibited a unique property of inducing the proliferation of cardiomyocytes. Hence, Example 15 was carried out in order to show the effectiveness of bFGF in cardiomyocytes derived from human ES cells and to review its effectiveness more closely by comparing it with other growth factors.

Basically, an α-MEM+ITS was used as a culture medium. This basal culture medium was supplemented with 25 ng/ml bFGF (Peprotech, Inc., Rocky Hill, N.J., USA), 25 ng/ml acidic FGF (aFGF), 25 ng/ml FGF-4, 20 ng/ml keratinocyte growth factor (KGF), 100 ng/ml stem cell factor (SCF), 100 ng/ml vascular endothelial growth factor (VEGF), 10 ng/ml leukemia inhibiting factor (LIF) (Millipore Corporation, Billerica, Mass., USA), 300 ng/ml glial cell line-derived neurotrophic factor (GDNF), 20 ng/ml hepatocyte growth factor (HGF), 10 ng/ml insulin-like growth factor (IGF)-1, 100 ng/ml epidermal growth factor (EGF), $1 \times 10^{-7}$ M endothelin-3 (ET-1), 10 ng/ml platelet derived growth factor (PDGF)-AA, or 100 ng/ml PDGF-BB (those reagents without the indication of where to obtain were all purchased from R&D systems). Human ES cells were cultured using each of the culture medium to prepare cell aggregates.

Figure 20A:
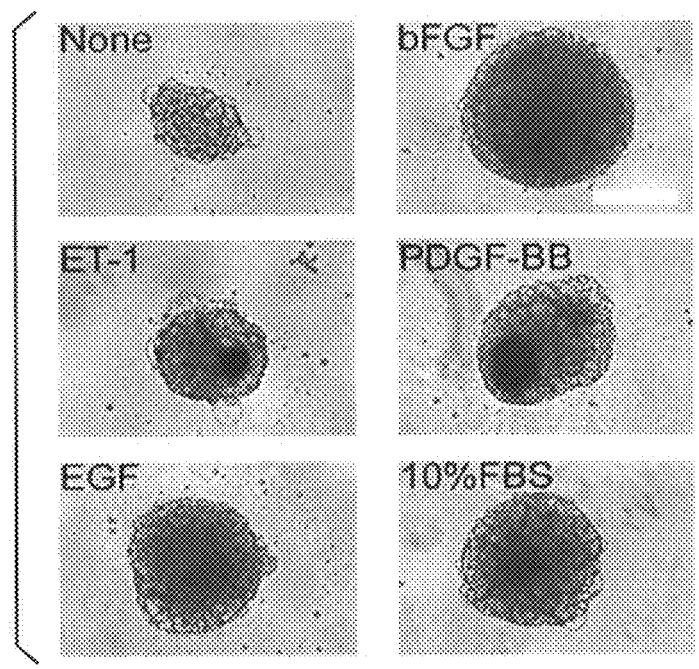
FIG. 20A shows the results of culturing purified, human ES cell-derived cardiomyocytes under serum-free conditions in the presence of added bFGF or other growth factors.
Figure 20B:
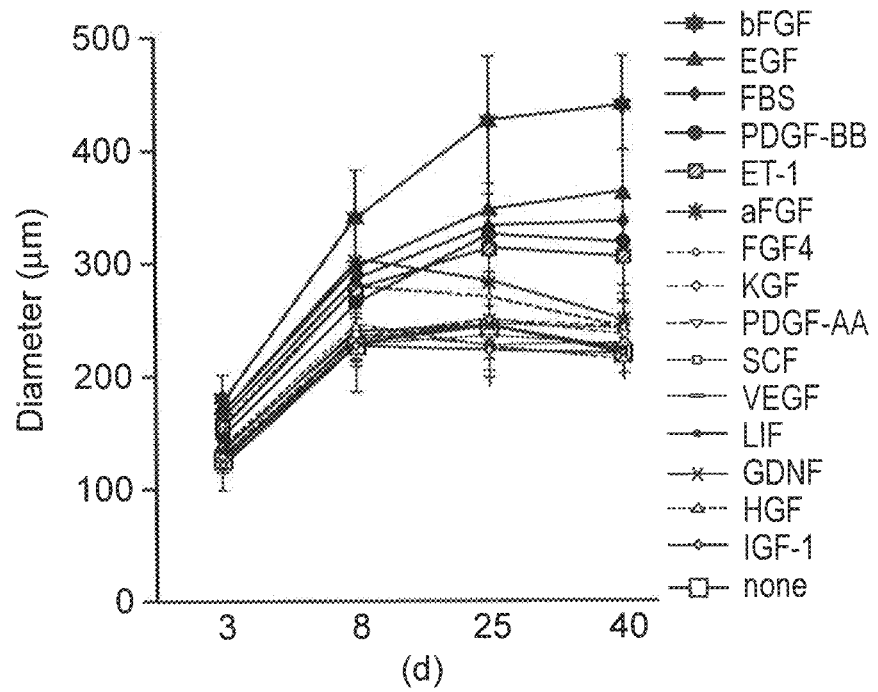
FIG. 20B shows that bFGF was preferential in the cell protecting and growth activating effects.

The diameter of cell masses was measured 3, 8, 25 and 40 days after the preparation of cell masses. As it turned out, the cell mass prepared in the presence of bFGF had the largest diameter on each of the clays (FIG. 20A). It was also found that this protecting action was continued as long as 40 days. Instead of bFGF, each of the various substances mentioned above was added to the culture medium and checked for their effect on the formation of cell masses: EGF, PDFG-BB and ET-1 were found to be effective, though not as effective as bFGF (FIG. 20B).

As a result, it turned out that, even in the case of differentiation of cardiomyocytes derived from human ES cell, bFGF has cell protecting and growth promoting activities under serum-free conditions and that these actions are stronger than those of other growth factors.

Figure 21:
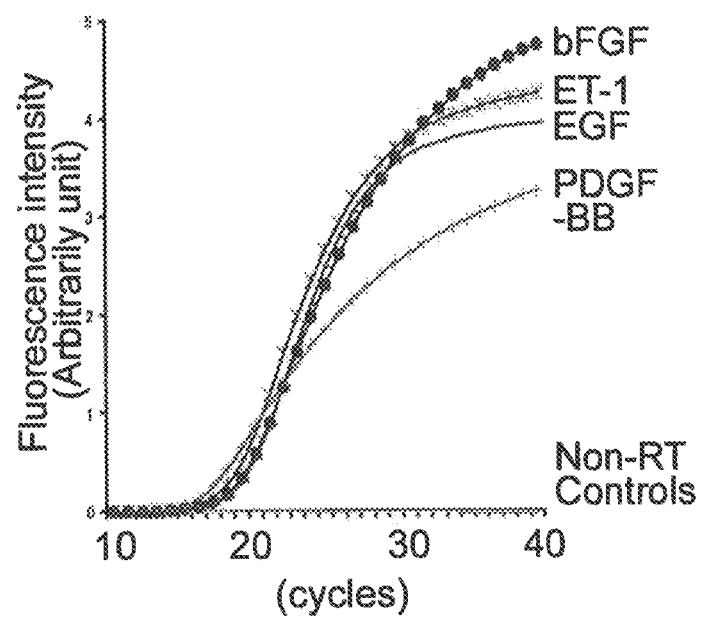
FIG. 21 shows the expression of genes for bFGF, EGF, PDGE-BB, and ET-1 in the host heart as it relates to the mechanism of maturation for the ease where cell masses of mouse cardiomyocytes remain engrafted in the host heart for a prolonged period of time.

Further, in order to elucidate the mechanism by which cardiomyocytes transplanted into the host heart can mature in the cardiac tissue after transplantation, bFGF, EGF, PDGF-BB and ET-1 were tested by real-time PGR (Applied Biosystems) for the possibility of gene expression in the host heart. The primers and probes for the respective genes were purchased from Applied Biosystems (TaqMan gene expression assays); to be more specific, bFGF (Mm0128715_ml), EGF (Mm01316967_ml), PDGF-BB (Mm01298577_ml), and ET-1 (Mm01351840_gl) were used. The reagents used for analysis and the operating procedure were in accordance with the instruction manual provided by Applied Biosystems. As a result, it turned out that the genes mentioned above were expressed in the host heart (FIG. 21).

The results of Example 15 suggested that the group of growth factors required for the survival and maturation of the cell masses of cardiomyocytes transplanted into the heart are supplied from the host heart.

INDUSTRIAL APPLICABILITY

According to the present invention, it has been found that cardiomyocytes derived from embryonic stem cell that have been purified by dispersing to single cells have such a new characteristic that they are capable of aggregating when they are cultured under serum-free conditions. By constructing cell masses using the method of the present invention, long-term culture can be performed with the survival rate or proliferative capacity of those cardiomyocytes being maintained at high levels. It has further been found that, when those cells are transplanted to the cardiac tissue of an individual (the living body), their engraftment rate in the cardiac tissue is significantly enhanced, with the result that the cardiomyocytes will not mix with non-cardiomyocytes but can be made engrafted for an extended period of time within the cardiac tissue. Thus, the present invention has enhanced the feasibility of providing cardiomyocytes for transplantation, as well as a method of cell therapy on the heart which is alternative to cardiac transplantation as a treatment, of cardiac disease by transplanting cardiomyocytes that have been prepared outside the living body, and a medical device comprising cell masses of cardiomyocytes.

The invention claimed is:

1. A method of treating myocardial infarction in a mammal comprising the steps of:
    a) differentiating isolated mammalian pluripotent stem cells into aggregated cell masses comprising cardiomyocytes;
    b) dispersing the aggregated cell masses comprising cardiomyocytes such that single cardiomyocytes are obtained;
    c) purifying the single cardiomyocytes of the step b);
    d) culturing the purified single cardiomyocytes in a culture medium under serum-free conditions for at least 12 hours such that the single cardiomyocytes form reaggregated masses of cardiomyocytes; and
    e) transplanting the reaggregated masses of cardiomyocytes into a site of myocardial infarction in the mammal such that a symptom of the myocardial infarction is treated.

2. The method of claim 1, wherein the step e) comprises injecting the reaggregated masses of cardiomyocytes into the cardiac tissue of the mammal at the site of the infarction.

3. The method of claim 1, wherein the mammalian pluripotent stem cells are selected from the group consisting of: embryonic stem cells, embryonic germ cells, germline stem cells, and induced pluripotent stem cells.

4. The method of claim 1, wherein the reaggregated masses of cardiomyocytes formed at the step d) have a spherical shape.

5. The method of claim 1, wherein the single cardiomyocytes are cultured under a suspension culture condition at the step d).

6. A method of treating myocardial infarction in a mammal comprising the steps of:
    a) differentiating isolated mammalian pluripotent stem cells into aggregated cell masses comprising cardiomyocytes;
    b) dispersing the aggregated cell masses comprising cardiomyocytes such that single cardiomyocytes are obtained;
    c) purifying the single cardiomyocytes of the step b);
    d) culturing the purified single cardiomyocytes in a culture medium under serum-free conditions for at least 12 hours such that the single cardiomyocytes form reaggregated masses of cardiomyocytes; and
    e) transplanting a sheet of the reaggregated masses of cardiomyocytes into a site of myocardial infarction in the mammal such that a symptom of the myocardial infarction is treated.

7. The method of claim 6, wherein the sheet of the reaggregated masses of cardiomyocytes has a thickness of 50-300 µm.

8. The method of claim 6, wherein the mammalian pluripotent stem cells are selected from the group consisting of: embryonic stem cells, embryonic germ cells, germline stem cells, and induced pluripotent stem cells.

9. The method of claim 6, wherein the reaggregated masses of cardiomyocytes formed at the step d) have a spherical shape.

10. The method of claim 6, wherein the single cardiomyocytes are cultured under a suspension culture condition at the step d).

11. A method of treating myocardial infarction in a mammal comprising the steps of:
    a) differentiating isolated mammalian pluripotent stem cells into aggregated cell masses comprising cardiomyocytes;
    b) dispersing the aggregated cell masses comprising cardiomyocytes such that single cardiomyocytes are obtained;
    c) purifying the single cardiomyocytes of the step b);
    d) culturing the purified single cardiomyocytes in a culture medium under serum-free conditions for at least 12 hours such that the single cardiomyocytes form reaggregated masses of cardiomyocytes;
    e) seeding the reaggregated masses of cardiomyocytes on a surface;
    f) maintaining a suspension culture of the seeded reaggregated masses of cardiomyocytes until a sheet of cardiomyocytes having a thickness of 50-300 µm is formed; and
    g) transplanting the sheet of cardiomyocytes into a site of myocardial infarction in the mammal such that a symptom of the myocardial infarction is treated.

12. The method of claim 11, wherein the mammalian pluripotent stem cells are selected from the group consisting of: embryonic stem cells, embryonic germ cells, germline stem cells, and induced pluripotent stem cells.

13. The method of claim 11, wherein the reaggregated masses of cardiomyocytes formed at the step d) have a spherical shape.

14. The method of claim 11, wherein the single cardiomyocytes are cultured under a suspension culture condition at the step d).

* * * * *